United States Patent [19]
Chiang et al.

[11] Patent Number: 5,839,442
[45] Date of Patent: Nov. 24, 1998

[54] PORTABLE ULTRASOUND IMAGING SYSTEM

[75] Inventors: Alice M. Chiang, Weston; Steven R. Broadstone, Woburn, both of Mass.

[73] Assignee: TeraTech Corporation, Burlington, Mass.

[21] Appl. No.: 496,805

[22] Filed: Jun. 29, 1995

[51] Int. Cl.$^6$ ............................................. A61B 8/00
[52] U.S. Cl. ............................................. 128/661.01
[58] Field of Search ................ 128/660.07, 660.08, 128/660.1, 661.01, 660.04, 660.05, 710; 73/620, 625, 626

[56] References Cited

U.S. PATENT DOCUMENTS

| | | | |
|---|---|---|---|
| 4,227,417 | 10/1980 | Glenn | 73/625 |
| 4,387,597 | 6/1983 | Brandestini | 128/661.01 |
| 4,401,957 | 8/1983 | McKeighen et al. | 333/165 |
| 4,809,184 | 2/1989 | O'Donnell et al. | 364/413.25 |
| 5,295,485 | 3/1994 | Shinomura et al. | 128/660.07 |
| 5,522,391 | 6/1996 | Beaudin et al. | |

FOREIGN PATENT DOCUMENTS

| | | |
|---|---|---|
| 0627635 A2 | 12/1994 | European Pat. Off. |
| 4241712 A1 | 6/1993 | Germany . |
| 4302538 C1 | 4/1994 | Germany . |
| 2219089 | 11/1989 | United Kingdom . |

*Primary Examiner*—George Manuel
*Attorney, Agent, or Firm*—Hamilton, Brook, Smith & Reynolds

[57] ABSTRACT

A portable ultrasound imaging system includes a hand-held scan head coupled by a cable to a portable battery-powered data processor and display unit, preferably in the form of a lap-top computer. The scan head enclosure houses an array of ultrasonic transducers and the circuitry associated therewith, including pulse synchronizer circuitry used in the transmit mode to time transmission of ultrasonic pulses and beam forming circuitry used in the receive mode to dynamically focus reflected ultrasonic signals returning from the region of interest being imaged. Because the pulse synchronizer and beam forming circuits are integrated on small chips, they can be included in the scan head, resulting in a portable low-power system. Also, since the beam forming and summation functions are performed in the scan head in proximity to the transducer elements, signal loss is substantially reduced, resulting in much higher image quality. In addition, the focused summed signal is transferred to the data processor and display unit by a cable which is far less sophisticated and expensive than the cables used in prior systems to transfer all of the transducer signals to a console signal processing unit.

32 Claims, 16 Drawing Sheets

(A) Optical System (B) Time Delay Focus (C) Phase Focus

PORTABLE ULTRASOUND IMAGING SYSTEM

BACKGROUND OF THE INVENTION

Conventional ultrasound imaging systems typically include a hand-held scan head coupled by a cable to a large rack-mounted console processing and display unit. The scan head typically includes an array of ultrasonic transducers which transmit ultrasonic energy into a region being imaged and receive reflected ultrasonic energy returning from the region. The transducers convert the received ultrasonic energy into low-level electrical signals which are transferred over the cable to the processing unit. The processing unit applies appropriate beam forming techniques such as dynamic focusing to combine the signals from the transducers to generate an image of the region of interest.

Typical conventional ultrasound systems can have transducer arrays which consist of 128 ultrasonic transducers. Each of the transducers is associated with its own processing circuitry located in the console processing unit. The processing circuitry typically includes driver circuits which, in the transmit mode, send precisely timed drive pulses to the transducer to initiate transmission of the ultrasonic signal. These transmit timing pulses are forwarded from the console processing unit along the cable to the scan head. In the receive mode, beam forming circuits of the processing circuitry introduce the appropriate delay into each low-level electrical signal from the transducers to dynamically focus the signals such that an accurate image can subsequently be generated.

A schematic block diagram of an imaging array 18 of N piezoelectric ultrasonic transducers 18(1)–18(N) as used in an ultrasound imaging system is shown in FIG. 1A. The array of piezoelectric transducer elements 18(1)–18(N) generate acoustic pulses which propagate into the image target (typically a region of human tissue) or transmitting media with a narrow beam. The pulses propagate as a spherical wave with a constant velocity. Acoustic echoes in the form of returning signals from image points P or reflectors are detected by the same array 18 of transducer elements or another receiving array and can be displayed in a fashion to indicate the location of the reflecting structure P.

The acoustic echo from the point P in the transmitting media reaches each transducer element 18(1)–18(N) of the receiving array after various propagation times. The propagation time for each transducer element is different and depends on the distance between each transducer element and the point P. This holds true for typical ultrasound transmitting media, i.e. soft bodily tissue, where the velocity of sound is constant. Thereafter, the received information is displayed in a manner to indicate the location of the reflecting structure.

In two-dimensional B-mode scanning, the pulses can be transmitted along a number of lines-of-sight as shown in FIG. 1A. If the echoes are sampled and their amplitudes are coded as brightness, a grey scale image can be displayed on a CRT. An image typically contains 121 such scanned lines at 0.75° angular spacing, forming a 90° sector image. Since the velocity of sound in water is $1.54 \times 10^5$ cm/sec, the round-trip time to a depth of 16 cm will be 208 $\mu$s. Thus, the total time required to acquire data along 121 lines of sight (for one image) is 25.1 ms. If other signal processors in the system are fast enough to keep up with this data acquisition rate, two-dimensional images can be produced at rates corresponding to standard television video. For example, if the ultrasound imager is used to view reflected or back scattered sound waves through the chest wall between a pair of ribs, the heart pumping can be imaged in real time.

The ultrasonic transmitter is typically a linear array of piezoelectric transducers 18(1)–18(N) (typically spaced half-wavelength apart) whose elevation pattern is fixed and whose azimuth pattern is controlled primarily by delay steering. The radiating (azimuth) beam pattern of a conventional array is controlled primarily by applying delayed transmitting pulses to each transducer element 18(1)–18(N) in such a manner that the energy from all the transmitters summed together at the image point P produce a desired beam shape. Therefore, a time delay circuit is needed in association with each transducer element 18(1)–18(N) for producing the desired transmitted radiation pattern along the predetermined direction.

For a given azimuth angle, as can be seen in FIG. 1B, there can be two different transmitting patterns: a "single-focus" and a "zone-focus" pattern. The single-focus method employs a single pulse focused at mid-range of the image line along a particular line of sight. In a single pulse mode, the azimuth focus depth can be electronically varied, but remains constant for any predetermined direction. In zone-focus operation, multiple pulses, each focused at a different depth (zone), are transmitted along each line of sight or direction. For multiple pulse operation, the array of transmitters is focused at M focal zones along each scan direction, i.e., a series of M pulses is generated, $P_0, P_1, \ldots, P_{M-1}$, each pulse being focused at its corresponding range $R_0, R_1, \ldots, R_{M-1}$, respectively. The pulses are generated in a repeated sequence so that, after start up, every Mth pulse either begins a look down a new direction or corresponds to the initial pulse $P_0$ to repeat the series of looks down the present direction. For the zone-focused mode, a programmable time-delay circuit is needed in association with each transducer element to produce beam patterns focused at different focal zones.

As previously described, the same array 18 of transducer elements 18(1)–18(N) can be used for receiving the return signals. The reflected or echoed beam energy waveform originating at the image point reaches each transducer element after a time delay equal to the distance from the image point to the transducer element divided by the assumed constant speed of the waveform of signals in the media. Similar to the transmitting mode, this time delay is different for each transducer element. At each receiving transducer element, these differences in path length should be compensated for by focusing the reflected energy at each receiver from the particular image point for any given depth. The delay at each receiving element is a function of the distance measured from the element to the center of the array and the viewing angular direction measured normal to the array. It should be noted that in ultrasound, acoustic pulses generated by each transducer are not wideband signals and should be represented in terms of both magnitude and phase.

The beam forming and focusing operations involve forming a sum of the scattered waveforms as observed by all the transducers, but in this sum, the waveforms must be differentially delayed so that they will all arrive in phase and in amplitude in the summation. Hence, a beam forming circuit is required which can apply a different delay on each channel, and vary that delay with time. Along a given direction, as echoes return from deeper tissue, the receiving array varies its focus continually with depth. This process is known as dynamic focusing.

FIGS. 2A–2C show schematic block diagrams of three different conventional imaging or beam focusing techniques.

A non-programmable physical lens acoustic system 50 using an acoustic lens 51 is shown in FIG. 2A. In turn, dynamic focusing systems where associated signal processing electronics are employed to perform real-time time delay and phase delay focusing functions are respectively shown in FIGS. 2B and 2C. FIG. 2B shows a time delay system 52 using time delay elements 53, and FIG. 2C shows a phase delay system 54 using phase delay elements 55.

In the lensless systems of FIGS. 2B and 2C, the signal processing elements 53, 55 are needed in association with each receiving transducer element, thus defining processing channels, to provide time delay and focus incident energy from a field point to form an image. Accordingly, a beam forming circuit is required which can provide a different delay on each processing channel, and to further vary that delay with time. Along a predetermined direction, as echoes return from distances further away from the array of transducer elements, the receiving array varies its focus continually with depth to perform dynamic focusing.

After the received beam is formed, it is digitized in a conventional manner. The digital representation of each received pulse is a time sequence corresponding to a scattering cross section of ultrasonic energy returning from a field point as a function of range at the azimuth formed by the beam. Successive pulses are pointed in different directions, covering a field of view from −45° to +45°. In some systems, time averaging of data from successive observations of the same point (referred to as persistence weighting) is used to improve image quality.

For example, in an ultrasound imaging system operating at a 2–5 MHz frequency range, an electronic circuit capable of providing up to 10 to 20 $\mu$s delay with sub-microsecond time resolution is needed for the desired exact path compensation. As shown in FIG. 2B, a delay line is inherently matched to the time-delay function needed for dynamic focusing in a lensless ultrasound system.

More specifically, in an exemplary ultrasound imaging system with a 5 MHz operating frequency and an array of 128 transducer elements on half-wavelength centers, a straightforward delay implementation requires each processing channel/transducer element to include either a 480-stage delay line with a clock period programmable with a 25 ns resolution or a 480-stage tapped delay line clocked at 40 MHz in conjunction with a programmable 480-to-one time-select switch to set the appropriate delay. There are two problems associated with these conventional techniques. First, a simple variable-speed clock generator has not been developed to date. Secondly, for an N-stage tapped delay line, the area associated with the tap select circuit is proportional to $N^2$, thus such a circuit would require a large amount of microchip area to realize an integrated tap architecture.

Due to the difficulty and complexity associated with the generation of the control circuits of the conventional approach, only a few time-delay structures could be integrated on one microchip, and therefore a large number of chips would be needed to perform a multi-element dynamic beam forming function. For these reasons, none of the prior art ultrasound imaging systems utilize the straightforward time-delay implementation. Instead, a plane-wave mixer approximation is used. In this approximation process, the total delay is separated into two parts: an analog plane-wave mixer technique is used to approximate the required fine delay time and a true coarsely spaced delay line is used to achieve the coarse delay time.

In accordance with the plane-wave approximation, the fine delay can be achieved by modifying the phase of AC waves received by each receiving processing channel and implemented by heterodyning the received waves from each receiving transducer element with different phases of a local oscillator, i.e., creating analog phase shifting at each processing channel. Specifically, by selecting a local oscillator with a proper phase angle of the form $\cos(\omega_0 t + \Omega_n(t))$ where $\Omega_n$ is chosen to satisfy the expression $\Omega_n(t) = \omega_0 ((T'_n(t) - T'_n(t))$ $T_n(t)$ is the ideal compensating delay and $T'_n(t)$ is a coarsely quantized approximation of $T_n$. It will be appreciated that when the mixer output is delayed by $T'_n$, the phase of one of its intermediate frequency (IF) sidebands provides phase coherence among all the processing channels.

In the conventional implementation of the aforementioned technique, a tap select is used which connects any received down-conversion mixer output to any tap on a coarsely spaced, serially connected delay line. The tap select is essentially a multiposition switch that connects its input to one of a number of output leads. One output lead is provided for each tap on the delay line. Therefore, each mixer output can be connected to a few coarsely spaced taps on a delay line, and all the tap outputs can be summed together coherently. However, for an exemplary 5 MHz operation, if a single-mixer arrangement as described above is used, a delay line with delay resolution less than one microsecond is needed.

In summary, the conventional technique described heretofore involves heterodyning the received signals with an oscillator output by selecting a local oscillator frequency so as to down convert the output to an IF frequency. This down converted signal is then applied to another mixer. By selecting the proper phase angle of the second oscillator, the phase of the intermediate frequency waves produced by the second heterodyning is controlled. The output of the second mixer is then connected through a tap select to only one or at the most a few coarsely spaced taps on a delay line during the focal scanning along each direction.

The aforementioned approximation technique is used due to the fact that given an image that is somewhat out of focus, the image can be focused in an economically feasible manner by utilizing readily available techniques such as analog mixers and RC networks. Unfortunately, the mixer approximation method suffers from image misregistration errors as well as signal loss relative to the ideally-focused (perfect delay) case.

Modern ultrasound systems require extensive complex signal processing circuitry in order to function. For example, hundreds of delay-and-sum circuits are needed for dynamic beam forming. Also, pulsed Doppler processors are needed for providing two-dimensional depth and Doppler information in color flow images, and adaptive filters are needed for clutter cancellation. Each of these application requires more than 10,000 MOPS (million operations per second) to be implemented. Even state-of-the-art CMOS chips only offer several hundred MOPS per chip, and each chip requires a few watts of electric power. Thus, an ultrasound machine with a conventional implementation requires hundreds of chips and dissipates hundreds of watts of power. As a result, conventional systems are implemented in the standard large rack-mounted cabinets.

Another drawback in conventional ultrasound systems is that the cable connecting the scan head to the processing and display unit is required to be extremely sophisticated and, hence, expensive. Since all the beam forming circuitry is located in the console, all of the low-level electrical signals from the ultrasonic transducers must be coupled from the scan head to the processing circuitry. Because the signals are of such a low level, they are extremely susceptible to noise, crosstalk and loss. With a typical transducer array of 128 transducers, the cable between the scan head and the processing and display console is required to contain 128 low-noise, low-crosstalk and low-loss coaxial cables. Such a cable requires expensive materials and extensive assembly time and is therefore very expensive.

SUMMARY OF THE INVENTION

The present invention is directed to a portable ultrasound imaging system and method. The imaging system of the invention includes a hand-held scan head coupled to portable processing circuitry by a cable. The scan head includes a housing which houses the array of ultrasonic transducers which transmit the ultrasonic signals into the region of interest being imaged and which receive reflected ultrasonic signals from the region of interest and which convert the received ultrasonic signals into electrical signals. The housing of the scan head also contains the beam forming circuitry used in the imaging system of the invention to combine the electrical signals from the ultrasonic transducers into an electronic representation of the region of interest. The electronic representation of the region of interest is forwarded over an interface via the system cable to data processing and display circuitry which uses the representation to generate an image of the region of interest.

In one embodiment, the portable processing circuitry is implemented in the form of a lap-top computer which can include an integrated keyboard, a PCMCIA standard modem card for transferring image data and a flip-top flat panel display, such as an active matrix LCD. The lap-top computer, and, therefore the entire system, can be powered by a small lightweight battery. The entire system, including scan head, cable and computer is therefore very lightweight and portable. The total weight of the system preferably does not exceed ten pounds.

In one embodiment, the system also includes an interface unit between the scan head and the lap-top computer. Instead of being connected directly to the computer, the system cable is connected to the interface unit. Another cable couples the interface unit to the computer. The interface unit performs control and signal/data processing functions not performed by the computer. This reduces the overall processing load on the computer.

To allow implementation of the functions of the ultrasound imaging system of the invention in the scan head, much of the signal processing circuitry associated with the ultrasonic transducers is integrated on small CMOS chips. For example, the beam forming circuitry used to introduce individual delays into the received ultrasonic signals can be implemented on a single chip for a 64-element array. Thus, two chips are used for 128-element systems. The pulse synchronizing circuitry used to generate transducer driving pulses can also be implemented on a chip. In addition, high voltage driver circuits used in the transmit mode to drive the transducers and preamplifying circuits and gain control circuits used in a receive mode to condition the electrical signals from the transducers can also be integrated on chips.

In one preferred embodiment of the invention, the signal processing circuitry in the scan head is implemented in low-power, high-speed CMOS technology. The integrated circuitry is also adapted to be operated at lower voltages than conventional circuitry. As a result, the power dissipated in the integrated circuitry and, consequently, the thermal effects caused thereby, are substantially lower than those of conventional circuits. In one embodiment, the total power dissipated in the scan head is less than two watts. This allows the temperature of the scan head to be maintained below 40° C. With such low power dissipation and temperature, the circuits can be implemented in the relatively small volume of the scan head housing without suffering any degradation in performance due to thermal effects. The patient being examined also suffers no potentially harmful thermal effects. Also, because the system requires comparatively little power, it can be powered by a battery located in the data processor and display unit.

As discussed above, in ultrasound systems, individual delays are typically introduced into each individual transmitted ultrasonic pulse and into each signal from each transducer indicative of received reflected ultrasonic energy. These individual delays are used to ensure that the image of the region of interest is properly focused. In a typical ultrasound imaging system, electronic circuitry capable of providing up to 10–20 $\mu$s delay with sub-microsecond time resolution is needed to provide precise signal path compensation. In one preferred embodiment of the present invention, this wide range of delays with fine resolution is provided by a dual-stage programmable tapped delay line using CCD technology. The first stage introduces a fine delay and the second stage introduces a coarse delay. The delays are controlled by tapping clock frequencies, the fine delay being controlled by a higher clock frequency than the coarse delay. In one embodiment, the fine delay clock frequency is set at eight times the ultrasound signal frequency, and the coarse delay clock frequency is set at one-tenth the fine delay clock frequency. The clock frequencies are separately controllable to facilitate varying the ultrasound signal frequency to vary imaging depth.

Such devices are described in a U.S. Patent Application entitled "Integrated Beam Forming and Focussing Processing Circuit for Use in an Ultrasound System," by Alice M. Chiang, filed on the same date as the present application. That patent application is incorporated herein by reference.

In one embodiment, the frequency of the ultrasound signals is variable to allow for imaging at varying depths. This can be accomplished by internal or external adjustment of transducer signal driving frequency. Alternatively, for wider variations in frequency, the system of the invention accommodates different scan heads having arrays which operate at different frequencies. Also, the scan head of the invention can be provided with a facility for changing arrays based on the desired operating frequency.

In another alternative preferred embodiment, an adaptive beam forming circuit is used instead of the dual-stage delay line to provide the required delays at the required resolution. In the adaptive beam forming technique, a feedback circuit senses summed received signals from a tapped delay line and generates correction signals. The correction signals are to control individual multiplier weights in the beam forming circuitry to adjust the summed signal and eliminate the effects of clutter and interference from the image.

As described above, after the beam forming circuits dynamically focus and sum the signals from the ultrasonic transducers, the summed signal is forwarded over the system cable to the data processing and display subsystem of the imaging system. The data processing subsystem includes, among other things, scan conversion circuitry for converting the polar coordinates of received ultrasonic signals to rectangular coordinates suitable for further processing such as display. The scan conversion process of the present invention provides a higher quality image and requires far less complex circuitry than that of prior systems.

In the scan conversion of conventional systems, the value of each point on the (x,y) coordinate system is computed from the values of the four nearest neighbors on the polar (r, θ) array by simple linear interpolation. This is accomplished by use of a finite state machine to generate the (x,y) traversal pattern, a bi-directional shift register to hold the (r, θ) data samples and a large number of digital logic and memory units to control the process and ensure that the correct samples of (r, θ) data arrive for interpolation at the right time for each (x,y) point since the (x,y) data points are received asynchronously.

In the present invention, hardware complexity and cost are reduced by using a number-theoretic scheme for reliably generating the (x,y) grid traversal path in natural order, i.e., using the (r, θ) samples as they are acquired. This provides greater flexibility and better fidelity to the actual medical data since it permits the array traversals to be designed so that they do not impose an unnatural image reconstruction scheme. The approach taken in the present invention provides greater flexibility in that multiple effective paths through the (x,y) array are possible. As a result, full advantage is taken of different ultrasound scan frequencies and, hence, imaging depth.

After the image data is scan converted, it is post processed in accordance with its eventual intended presentation format. For example, the data can be digitized and formatted for presentation on a display. Alternatively, the (x,y) data values can be presented to a video compression subsystem which compresses the data to allow for data transmission to remote sites by modem or other known communication means.

The ultrasound imaging system of the invention also allows for imaging of moving objects by including a pulsed Doppler processing subsystem. Data from the beam forming circuitry is forwarded to the pulsed Doppler processor to generate data used to image the moving object. For example, the pulsed Doppler processor can be used to produce color flow map images of blood flowing through tissue.

The ultrasound imaging system of the invention has several advantages over prior conventional systems. Because much of the signal processing circuitry is integrated on small chips, the signal processing can be carried out in the scan head. Because of the proximity of the transducers to the processing circuitry, signal loss is substantially reduced. This results in greatly improved system performance in the form of high-resolution high-quality images. Also, since the signal summing is also performed in the scan head, only a single or very few cable conductor lines are required to transmit image signals to the data processing circuitry. The required cable is far less complex and expensive than that used in conventional systems.

The portability of the imaging system of the invention is also a very important asset. As described above, the system includes a small hand-held scan head, a small cable and a portable data processing and display unit such as a lap-top computer. It can be battery powered and hence can easily be carried to persons needing immediate attention at remote locations to perform quick diagnostic evaluation. By using the video data compression of the invention, the image data gathered at a remote site can be transferred by modem or wireless cellular link or other known means to a hospital for evaluation. Treatment instructions can then be relayed back to the operator where the patient can be administered treatment immediately.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
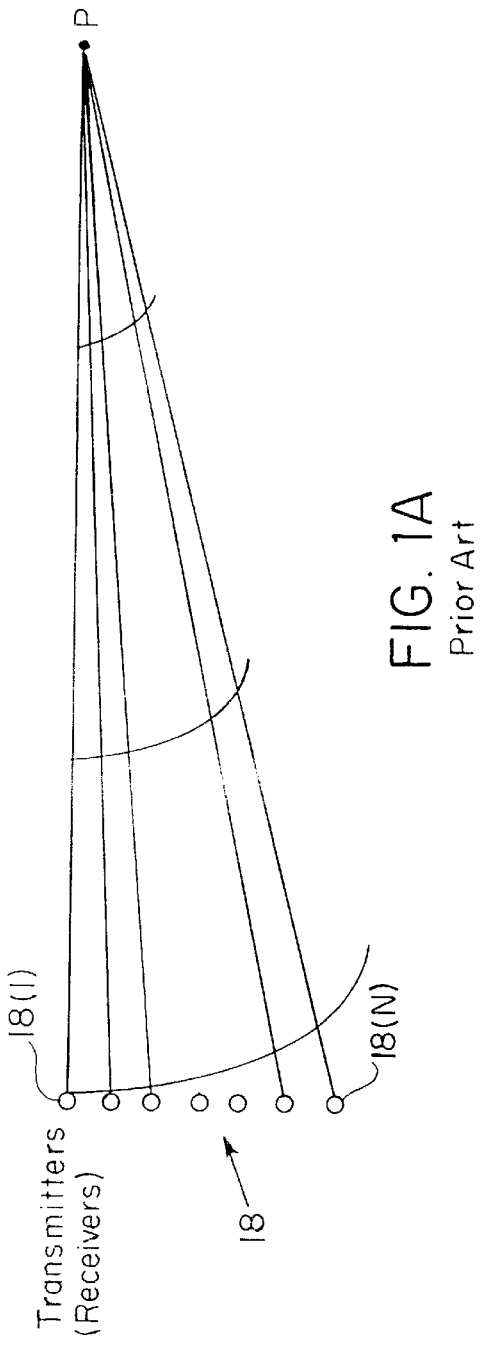
FIGS. 1A and 1B respectively show a block diagram of a conventional imaging array as used in an ultrasound imaging system and associated transmitting pulse patterns of a single pulse and multiple pulses in a zone-focused mode.
Figure 1B:
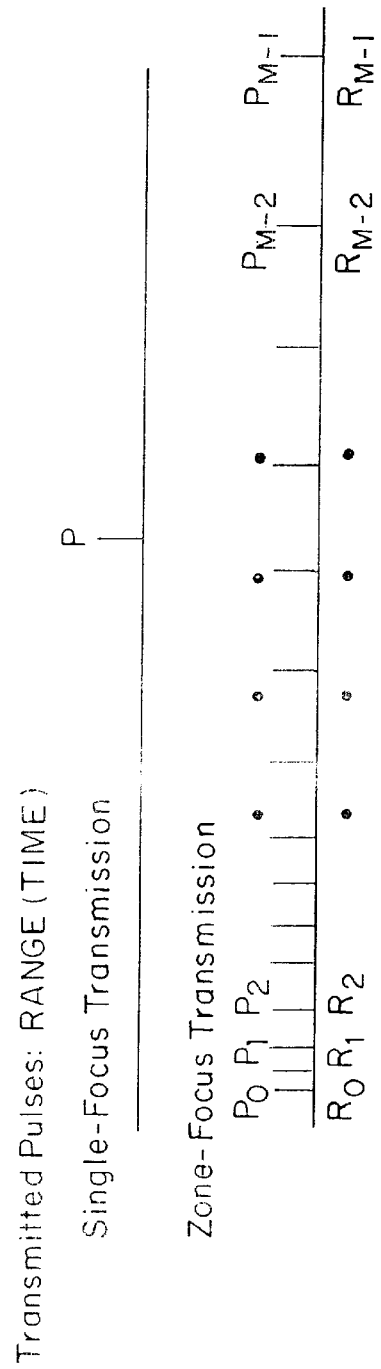
Figure 2A:
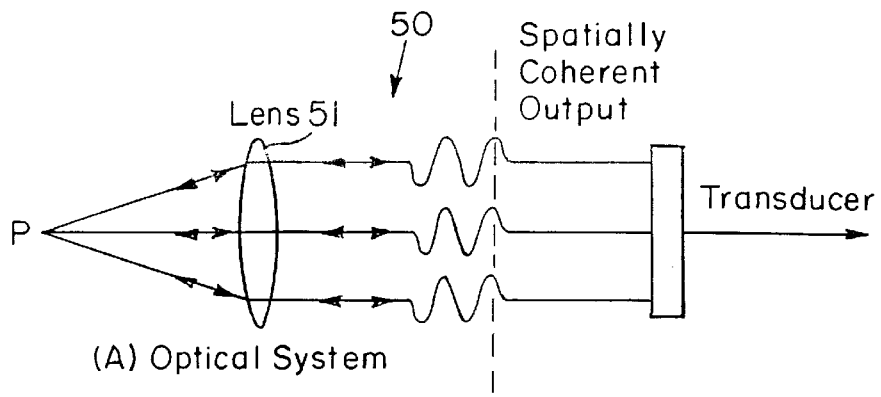
FIGS. 2A–2C respectively show block diagrams of three different conventional imaging or beam focusing techniques involving optical lens, time delay and phase delay operations.
Figure 2B:
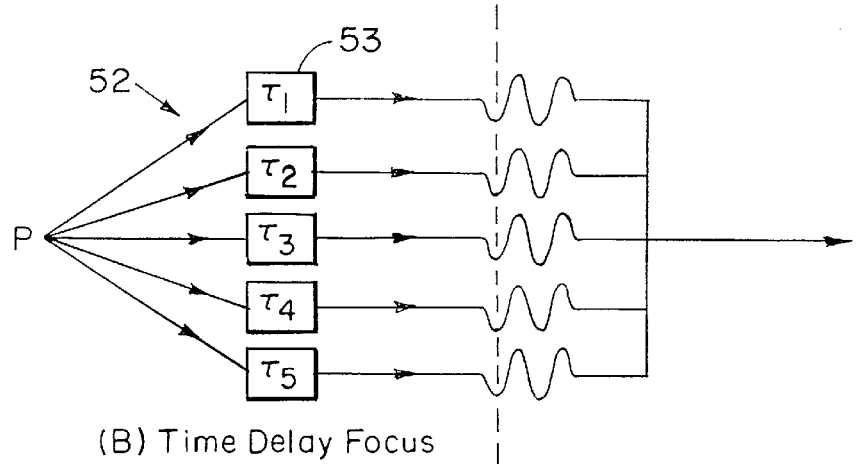
Figure 2C:
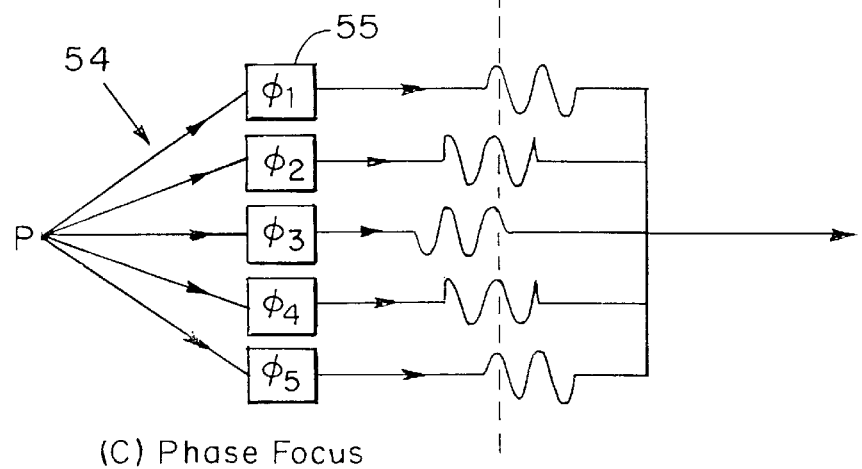
Figure 3:
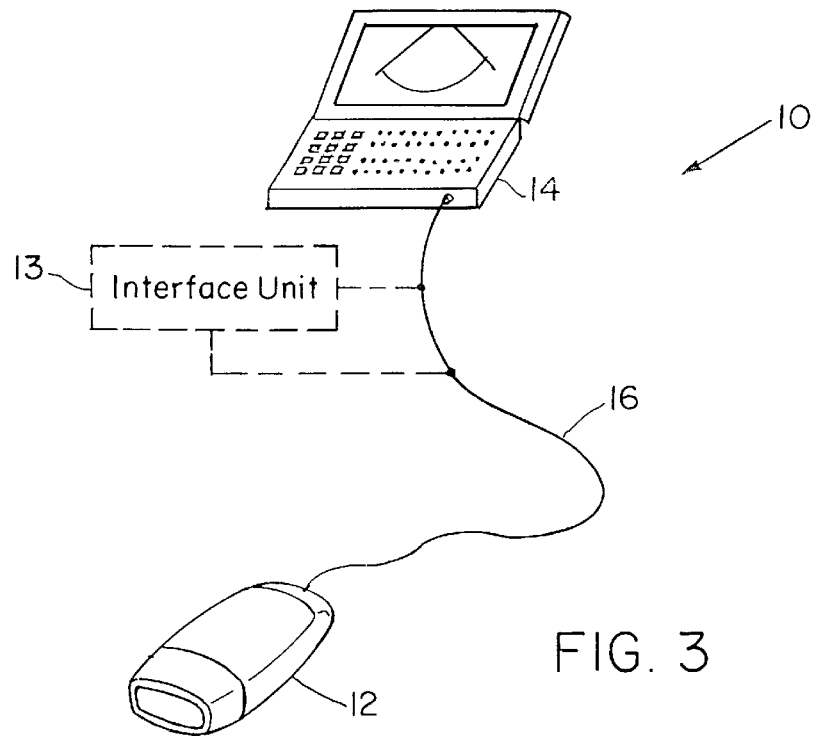
FIG. 3 is a schematic pictorial view of a preferred embodiment of the ultrasound imaging system of the present invention.

FIG. 3 is a schematic pictorial view of the ultrasound imaging system 10 of the present invention. The system includes a hand-held scan head 12 coupled to a portable data processing and display unit 14 which can be a lap-top computer. The scan head 12 is connected to the data processor 14 by a cable 16. In an alternative embodiment, the system 10 includes an interface unit 13 (shown in phantom) coupled between the scan head 12 and the data processing and display unit 14. The interface unit 13 preferably contains controller and processing circuitry including a digital signal processor (DSP). The interface unit 13 performs required signal processing tasks and provides signal outputs to the data processing unit 14 and/or scan head 12.

Figure 4:
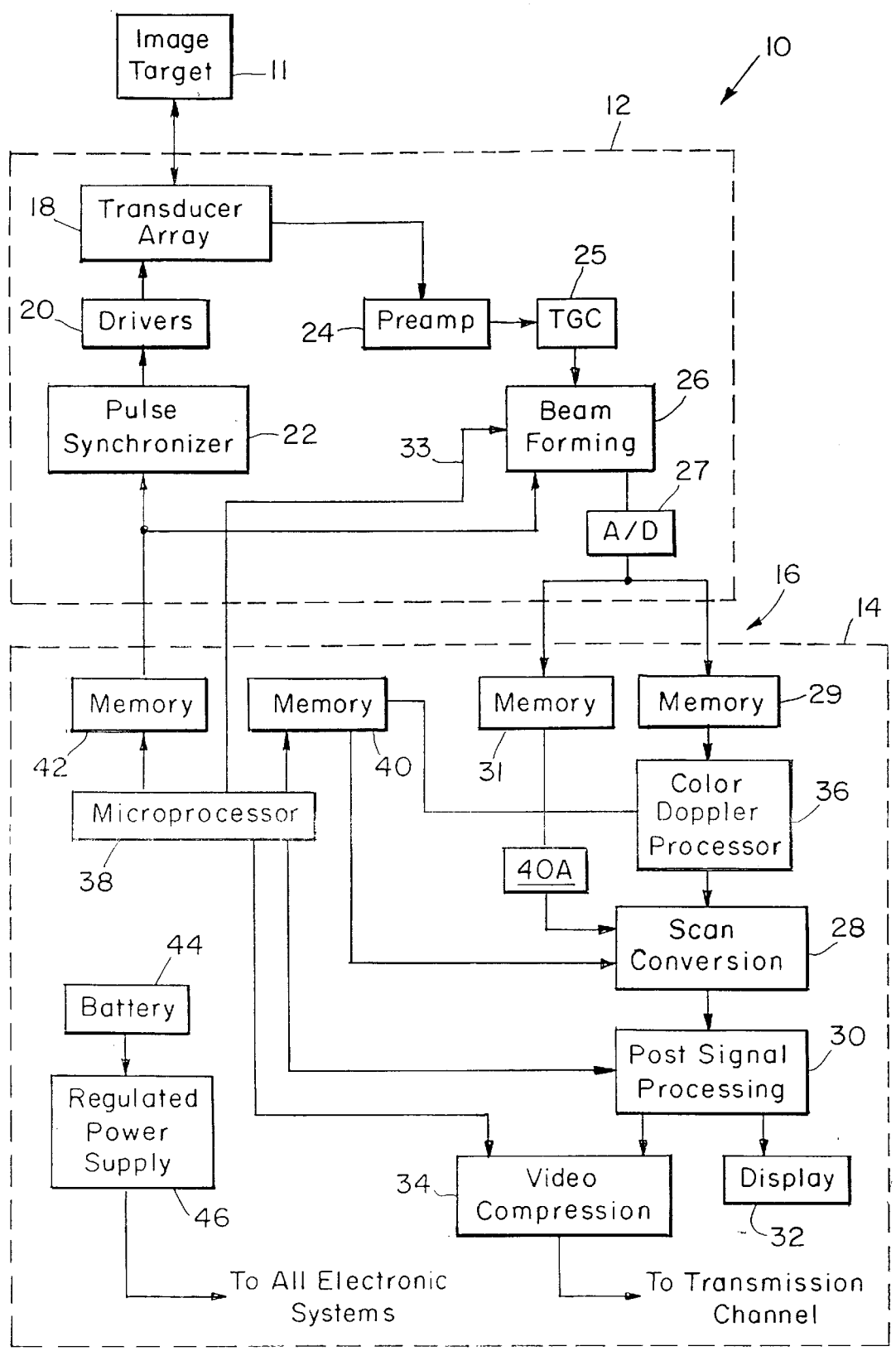
FIG. 4 is a schematic functional block diagram of a preferred embodiment of the ultrasound imaging system of the invention.

FIG. 4 is a schematic functional block diagram of the ultrasound imaging system 10 of the invention. As shown in FIG. 4, the scan head 12 includes an ultrasonic transducer array 18 which transmits ultrasonic signals into a region of interest or image target 11 such as a region of human tissue and receives reflected ultrasonic signals returning from the image target. The scan head 12 also includes transducer driver circuitry 20 and pulse synchronization circuitry 22. The pulse synchronizer forwards a series of precisely timed and delayed pulses to high voltage driver circuits in the drivers 20. As each pulse is received by the drivers 20, the high-voltage driver circuits are activated to forward a high-voltage drive signal to each transducer in the transducer array 18 to activate the transducer to transmit an ultrasonic signal into the image target 11.

Ultrasonic echoes reflected by the image target 11 are detected by the ultrasonic transducers in the array 18. Each transducer converts the received ultrasonic signal into a representative electrical signal which is forwarded to preamplification circuits 24 and time-varying gain control (TGC) circuitry 25. The preamp circuitry 24 sets the level of the electrical signals from the transducer array 18 at a level suitable for subsequent processing, and the TGC circuitry 25 is used to compensate for attenuation of the sound pulse as it penetrates through human tissue and also drives the beam forming circuits 26 (described below) to produce a line image. The conditioned electrical signals are forwarded to the beam forming circuitry 26 which introduces appropriate differential delay into each of the received signals to dynamically focus the signals such that an accurate image can be created. The signals delayed by the beam forming circuitry 26 are summed to generate a single signal which is forwarded over the cable 16 to the data processor and display unit 14. The details of the beam forming circuitry 26 and the delay circuits used to introduce differential delay into received signals and the pulses generated by the pulse synchronizer 22 will be described below in detail.

In one preferred embodiment, the dynamically focused and summed signal is forwarded to an A/D converter 27 which digitizes the summed signal. Digital signal data is then forwarded from the A/D 27 over the cable 16 to buffer memories 29 and 31. It should be noted that the A/D converter 27 is not used in an alternative embodiment in which the analog summed signal is sent directly over the system cable 16. The A/D converter 27 is omitted from further illustrations for simplicity.

Data from buffer memory 31 is forwarded to scan conversion circuitry 28 in the data processing unit 14. The scan conversion circuitry 28 converts the digitized signal data from the beam forming circuitry 26 from polar coordinates (r, θ) to rectangular coordinates (x,y). After the conversion, the rectangular coordinate data is forwarded to post signal processing stage 30 where it is formatted for display on the display 32 or for compression in the video compression circuitry 34. The video compression circuitry 34 will be described below in detail.

Digital signal data is forwarded from buffer memory 29 to a pulsed Doppler processor 36 in the data processor unit 14. The pulsed Doppler processor 36 generates data used to image moving target tissue 11 such as flowing blood. In the preferred embodiment, with pulsed Doppler processing, a color flow map is generated. The pulsed Doppler processor 36 forwards its processed data to the scan conversion circuitry 28 where the polar coordinates of the data are translated to rectangular coordinates suitable for display or video compression.

A control circuit preferably in the form of a microprocessor 38 controls the operation of the ultrasound imaging system 10. The control circuit 38 controls the differential delays introduced in both the pulsed synchronizer 22 and the beam forming circuitry 26 via a memory 42 and a control line 33. In one embodiment, the differential delays are introduced by programmable tapped CCD delay lines to be described below in detail. The delay lines are tapped as dictated by data stored in the memory 42. The microprocessor 38 controls downloading the coarse and fine delay line tap data from memory 42 to on-chip memories in both the pulsed synchronizer 22 and the beam forming circuitry 26.

The microprocessor 38 also controls a memory 40 which stores data used by the pulsed Doppler processor 36 and the scan conversion circuitry 28. It will be understood that memories 40 and 42 can be a single memory or can be multiple memory circuits. The microprocessor 38 also interfaces with the post signal processing circuitry 30 and the video compression circuitry 34 to control their individual functions. The video compression circuitry 34 as described below in detail compresses data to permit transmission of the image data to remote stations for display and analysis via a transmission channel. The transmission channel can be a modem or wireless cellular communication channel or other known communication means.

The portable ultrasound imaging system 10 of the invention can preferably be powered by a battery 44. The raw battery voltage out of the battery 44 drives a regulated power supply 46 which provides regulated power to all of the subsystems in the imaging system 10 including those subsystems located in the scan head 12. Thus, power to the scan head is provided from the data processing and display unit 14 over the cable 16.

Figure 5:
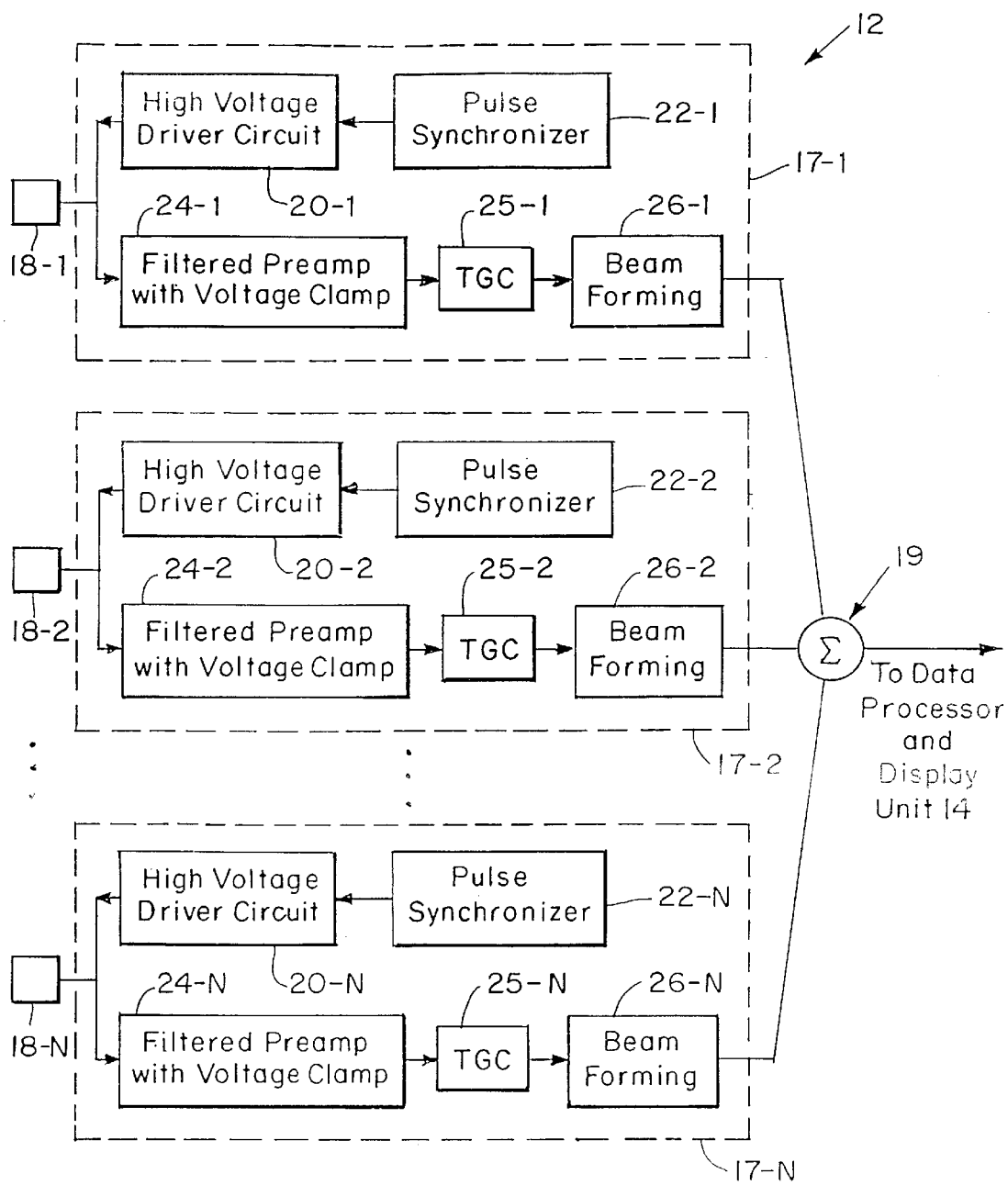
FIG. 5 is a schematic functional block diagram of a preferred embodiment of the ultrasound scan head of the present invention.

FIG. 5 is a detailed schematic functional block diagram of the scan head 12 used in the ultrasound imaging system 10 of the invention. As described above, the scan head 12 includes an array of ultrasonic transducers labeled in FIG. 3 as 18-(1), 18-(2), . . . ,18-(N), where N is the total number of transducers in the array, typically 128. Each transducer 18(1)–18(N) is coupled to a respective processing channel 17(1)–17(N).

Each processing channel 17(1)–17(N) includes a respective pulsed synchronizer 22(1)–22(N) which provides timed activation pulses to a respective high voltage driver circuit 20(1)–20(N) which in turn provides a driving signal to a respective transducer 18(1)–18(N) in the transmit mode. Each processing channel 17(1)–17(N) also includes respective filtered preamplification circuits 24(1)–24(N) which include voltage clamping circuits which, in the receive mode, amplify and clamp signals from the transducers 18(1)–18(N) at an appropriate voltage level. The time varying gain control circuitry (TGC) 25(1)–25(N) controls the level of the signals, and the beam forming circuitry 26(1)–26(N) performs dynamic focusing of the signals by introducing differential delays into each of the signals as described below in detail. The outputs from beam forming circuits 26(1)–26(N) are summed at a summing node 19 to generate the final focused signal which is transmitted over the cable 16 to the data processor and display unit 14 for subsequent processing.

In the present invention, one embodiment of the beam forming and focusing circuit 26 can be integrated on a single microchip and utilizes cascaded charge-coupled device (CCD) tapped delay lines to provide individual coarse and fine delays resulting in a wide range of delays with fine time resolution. This embodiment of the beam forming system of the invention, referred to herein as charge domain processing (CDP) circuitry, includes a plurality of processing circuits which, in a receiving mode, differentially delay signals representative of image waveforms received as reflected ultrasonic energy from the target object in order to generate a focused image. In a transmitting mode, the processing circuits differentially delay signals, which are to be transmitted as ultrasonic energy to a target object by the array 18 of transducers 18(1)–18(N), in order to generate a focused directional beam.

Each of the processing circuits includes a first delay line having a plurality of delay units operable in the receiving mode for receiving an image waveform and converting same into sampled data such as charge packets. In the transmitting mode, the first delay line receives the imaging signals and converts same into sampled data such as charge packets. A selection control circuit is operable for reading the sampled data from a selected first delay unit of the first delay line so as to correspond to a selected first time delay to accommodate fine delay resolution of the image waveform or imaging signals. A second delay line having a plurality of delay units is operable for sensing the sampled data from the selected first delay unit. The control circuit is further operable for reading the sampled data from a selected second delay unit of said second delay line so as to correspond to a selected second delay time to accommodate coarse delay resolution of the image waveform or imaging signals.

In the receiving mode, a summation circuit is provided for summing the sampled data from each of the selected second delay units in each of the processing circuits in order to produce a focused image. In the transmitting mode, an output circuit is provided for converting the sampled data from each of the selected second delay units in each of the processing circuits into signals representative of the focused directional beam.

The beam forming and focusing operations involve forming a summation of the waveforms as observed by all of the transducer elements. However, in this summation, the waveforms must be differentially delayed so that they all arrive in phase at a summation circuit 19 (see FIG. 5). Accordingly, each beam forming circuit 26 in accordance with the present invention provides a different time delay on each processing channel, and further varies that delay with time. The signals which are added in phase to produce a focused signal are then forwarded to the data processor and display unit 14.

For each nominal scanning direction, the differential delay required for information received by a transducer element 18(k) in the array, relative to the first element 18(1), varies predominantly with k, with a small correction as a function of time to correct focus for depth. The overall control of delay can involve very fine time resolution as well as a large range of delays. However, for a selected beam forming direction, this set of delays is achieved by a combination of a coarse delay in each channel to approximately compensate for direction, and a fine delay for each channel which combines the functions of focusing and refining the original coarse correction.

Figure 6:
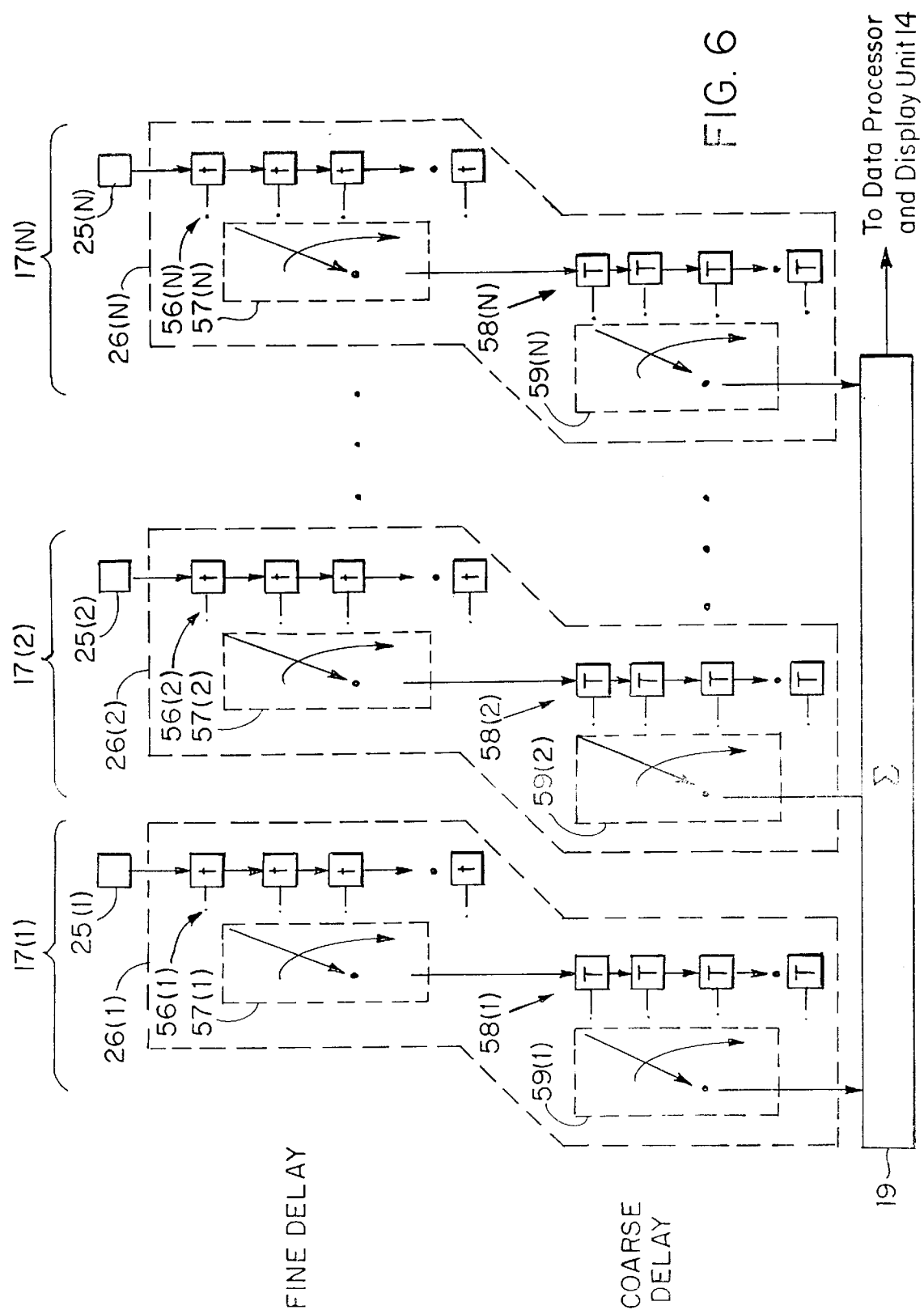
FIG. 6 shows an operational block diagram of an array of the beam forming and focusing circuits in accordance with the present invention.

According to one preferred embodiment of the beam forming circuitry 26 shown in operational block diagram form in FIG. 6, each of the beam forming circuits 26 is respectively arranged in a predetermined one of the N-parallel processing channels 17(1)–17(N), one for each of the array of transducer elements 18(1)–18(N). Each beam forming circuit 26 includes two cascading tapped delay lines 56(1)–56(N), 58(1)–58(N). Each circuit 26 receives as an input a signal from a TGC circuit 25 (see FIG. 3). The first delay line 56 in each channel provides a fine time delay for its received signal, while the cascaded second delay line 58 provides a coarse time delay. Each fine delay line has an associated programmable tap-select circuit 57(1)–57(N), and each coarse delay line has a programmable tap-select circuit 59(1)-59(N), both of which will be described in more detail hereinafter. The tap-select circuits are operable for effecting a variable delay time as a function of tap location.

During the operation of the circuits 26, signals which are received by each transducer element 18 are applied continuously to the input of its corresponding processing channel 17. The input signals to each processing channel are converted into a sequence of sampled data for initial propagation through the respective fine tapped delay lines 56. In accordance with a preferred embodiment of the present invention, both the fine 56 and coarse 58 tapped delay lines are charge-coupled device (CCD) tapped delay lines. Exemplary programmable CCD tapped delay lines are described in, for example, Beynon et al., *Charge-coupled Devices and Their Applications*, McGraw-Hill (1980), incorporated herein by reference. Accordingly, in the exemplary configuration of the processing circuit 26 using CCD delay lines, the input signals to each of the processing channels are converted to a sequence of charge packets for subsequent propagation through the fine and coarse delay lines.

At a predetermined time, which is dependent on the tap location selected by the system 10, a delayed sample is either destructively or nondestructively sensed from the selected tap of the fine delay line 56. The delayed sample is in turn input to the front end of the corresponding coarse delay line 58. The selected delay samples thereafter propagate through the coarse delay line, and are again destructively or nondestructively sensed at a properly selected tap location corresponding to a predetermined time delay designated in accordance with the operation of the ultrasound imaging system 10. The sensed sampled data from the coarse delay line of each processing channel is simultaneously summed by a summation circuit 19 to form the output beam.

Figure 7:
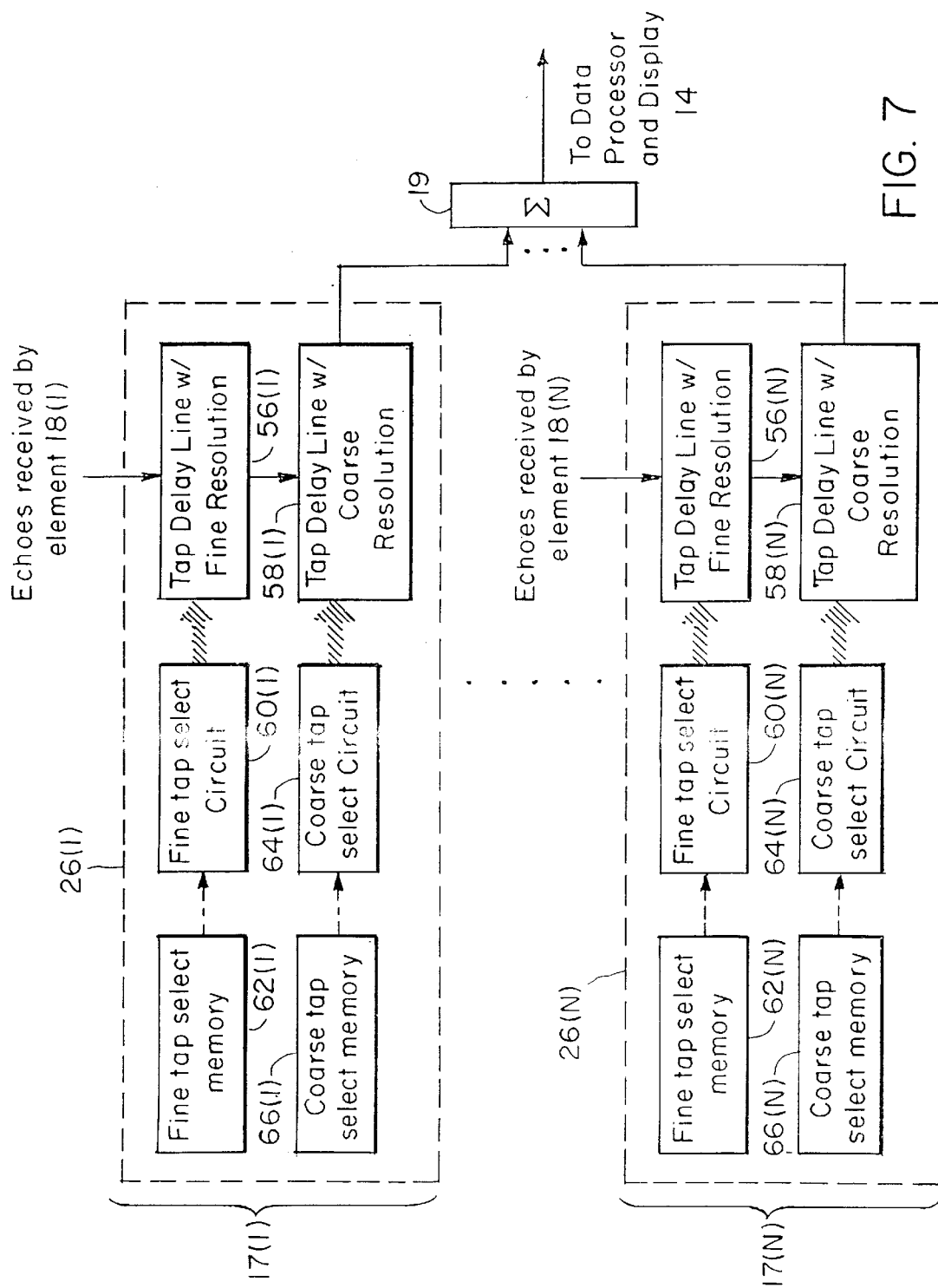
FIG. 7 shows a more detailed operational block diagram of an array of the beam forming and focusing circuits in accordance with the present invention.

With reference now to FIG. 7, a more detailed operational block diagram of the beam forming circuits 26(1)–26(N) of the present invention is shown. As illustrated, the programmable tap-select circuits 57(1)–57(N) for the fine delay lines each include respective fine tap select circuits 60(1)–60(N) and fine tap select memory units 62(1)–62(N). In turn, the programmable tap-select circuits 59(1)–59(N) for the coarse delay lines each include respective coarse tap select circuits 64(1)–64(N) and coarse tap select memory units 66(1)–66(N).

In accordance with a preferred embodiment of the beam forming circuits, the fine and coarse delay lines have differing clock rates. The fine delay line is clocked at a higher rate than the coarse delay line and is therefore capable of providing a much finer delay time than that of the coarse delay line. For instance, in an exemplary configuration, each circuit 26 has a 32-stage fine tapped delay line clocked at 40 MHz and a 32-stage coarse-tapped delay line clocked at 2 MHz. Such a configured circuit can provide up to a 16 µs delay with a programmable 25 ns delay resolution. In contrast, it will be appreciated that if a single delay line were used, it would require approximately 640 stages of delays. Furthermore, due to the cascaded delay line structure of the beam forming circuits of the present invention, a local memory of 5-bit wide by 64-stage is adequate for providing the dynamic focusing function for a depth up to 15 cm. However, if a single delay structure were used, it would require a local memory of 640-bit wide by 1280-stage long.

During operation of an individual beam forming circuit 26, the fine delay line taps are changed continuously by the microprocessor 38 via the memory 42 (see FIG. 4) during each echo receiving time to provide dynamic focusing. The fine tap select circuit 60, in the form of a digital decoder, and the local fine tap select memory 62 are used to select the desired tap position of the fine delay line 56. For example, the microprocessor instructs the memory 42 to download a data word to memory 62 to provide a digital address representative of the selected tap position to the select circuit 60 for decoding. In turn, the select circuit 60 effects the sampling of data from the selected tap. In an exemplary embodiment, a 5-bit decoder is used to provide a 32-tap selection.

The tap position of the coarse delay line 58 is set once before each echo return and is not changed during each azimuth view direction. As with the operation of the fine delay line, the coarse tap select circuit 64, in the form of a digital decoder, is used in conjunction with the local coarse tap select memory 66 to select the desired tap position of the coarse delay line.

Figure 8:
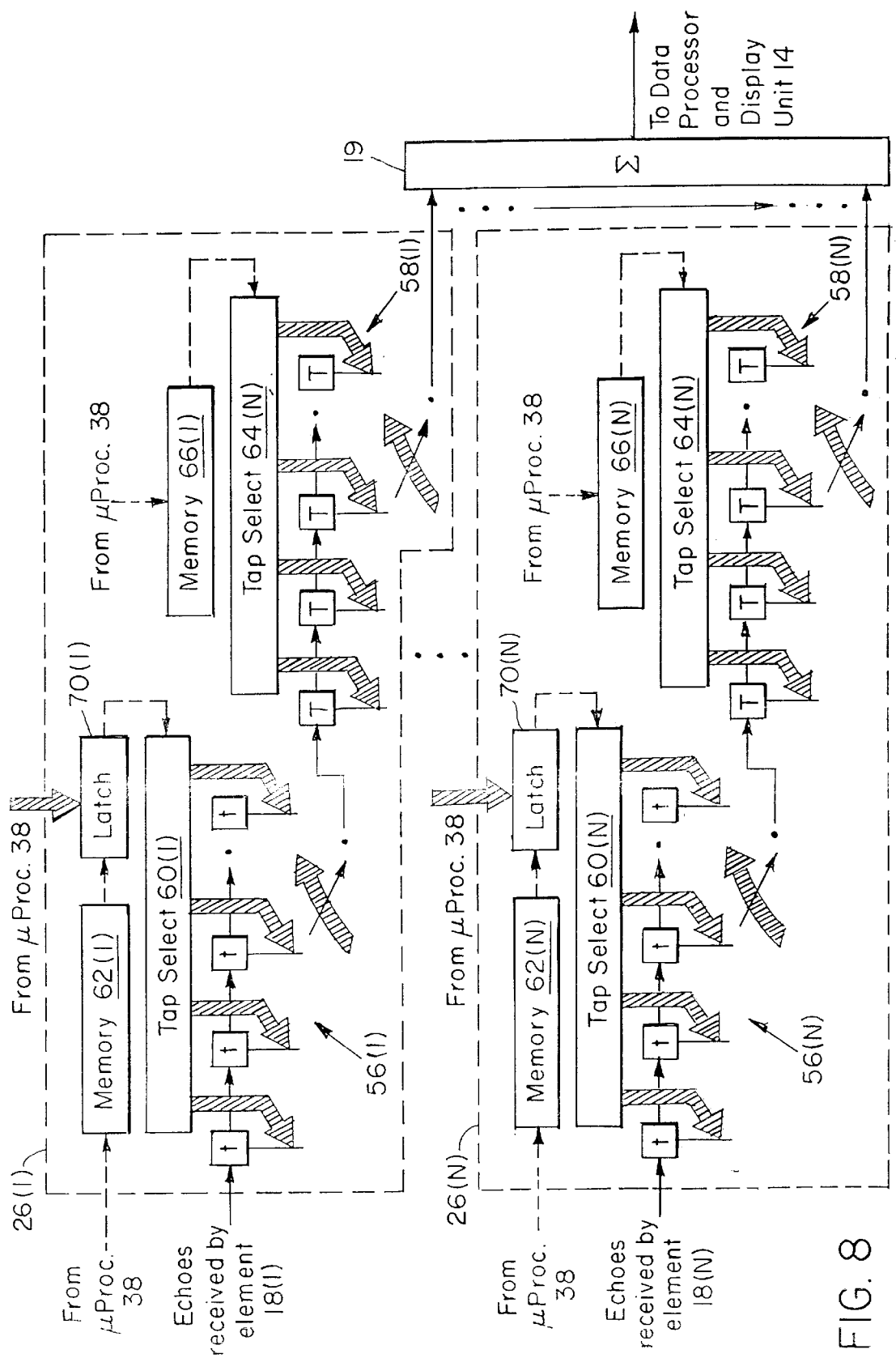
FIG. 8 shows an operational block diagram of an alternative embodiment of the present invention in which each of the beam forming and focusing circuits incorporates a latching circuit.

FIG. 8 shows an operational block diagram of an alternative embodiment of the beam forming circuitry 26 of the present invention in which each circuit 26 includes a respective latching circuit 70(1)–70(N) that generates a tap setting signal to each of the fine tap select circuits 60(1)–60(N). When the tap setting signal is provided to the fine tap select circuits, the tap selection will be fixed at the last tap of the fine tap delay lines (i.e. focusing point), thus the dynamic focusing function is not operable. This operation is controlled by the imaging system in situations where, for example, the imaging point is at a distance from the transducer elements which does not require a precise fine delay time. In this manner, the size of the fine tap select memory 62 is reduced.

Figure 9:
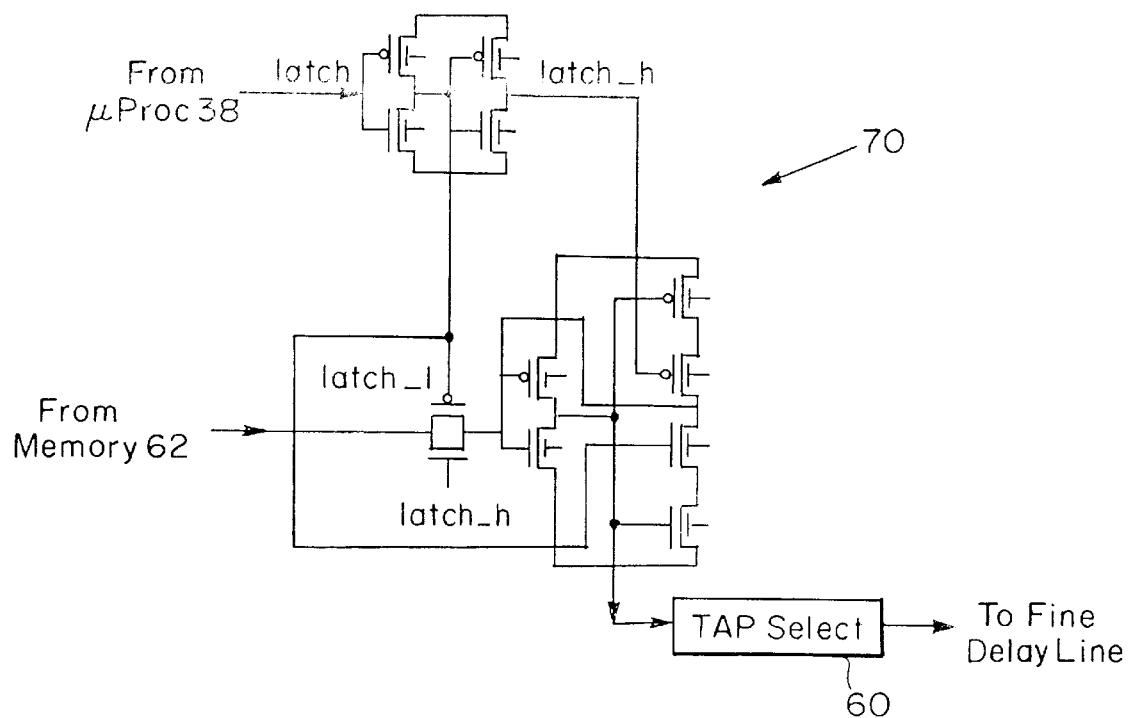
FIG. 9 shows a schematic block diagram of an exemplary embodiment of the latching circuit used in accordance with the present invention.

An exemplary embodiment of the latching circuit 70 in accordance with the present invention is shown in FIG. 9. In operation, when the latch is set high by the microprocessor 38, digital data from the memory 62 will pass through the CMOS passing transistors, and the defined transistor inverter provides an input to the appropriate tap select circuit (decoder) 60 so as to implement the dynamic focusing function. In contrast, when the latch is set low, the passing transistors are disabled, and thus the inverter output will be latched to the last data address in the memory, i.e., the last tap select position.

Using a 1.2 µm CCD/CMOS fabrication process provided by a conventionally known silicon foundry, Orbit Semiconductor, Inc., a prototype 10-channel beam forming microchip based on the fine/coarse delay architecture described above has been designed and fabricated. Due to the compactness of each fine and coarse delay line, and the simplification of its corresponding control circuits, this approach accommodates configuring the beam forming electronics of a 64-element receiver array to be integrated on one single microchip.

In the prototypical beam forming microchip, each processing circuit includes two cascaded programmable tapped delay lines (each 16-stages long), two 4-bit CMOS decoders and a 4×64-bit local memory for storing the tap locations. The prototype is configured with 10 processing channels, each of which includes the processing circuit of the present invention fabricated on a single silicon microchip. Each processing circuit can provide up to 10 µs of programmable delay with a 25 ns delay resolution. The beam forming chip operates such that at each azimuth viewing angle, echo return signals from an image point at a given range resolution received by a transducer element are sampled by the corresponding processing channel. Each processing circuit provides ideally compensated delays to each received return signal. All of the delayed outputs are then summed together to form a single beam or a focused image point. The chip area associated with each processing channel is only 500× 2000 µm$^2$. It follows that the dynamic beam forming electronics for a 64-element receiver array can be integrated in a single microchip with chip area as small as 64 mm$^2$, which corresponds to at least three to four order of magnitude size reduction compared to conventional devices.

The fine-coarse tapping architecture of the present invention accommodates a 12 µs delay with a 25 ns resolution with the two cascaded CCD tapped delay lines. Specifically, the architecture includes a first 16-stage long delay line clocked at 40 MHz and a second 32-stage long delay line clocked at 2 MHz. The shorter delay lines and the simplicity of the tapping circuit associated with these shorter delay lines allows all of the image-generating electronics to be integrated on a single chip. A single chip performs the electronic focus function for a 128-element array with more than two orders of magnitude reduction in chip area, power consumption and weight when compared with conventional implementations.

Figure 10:
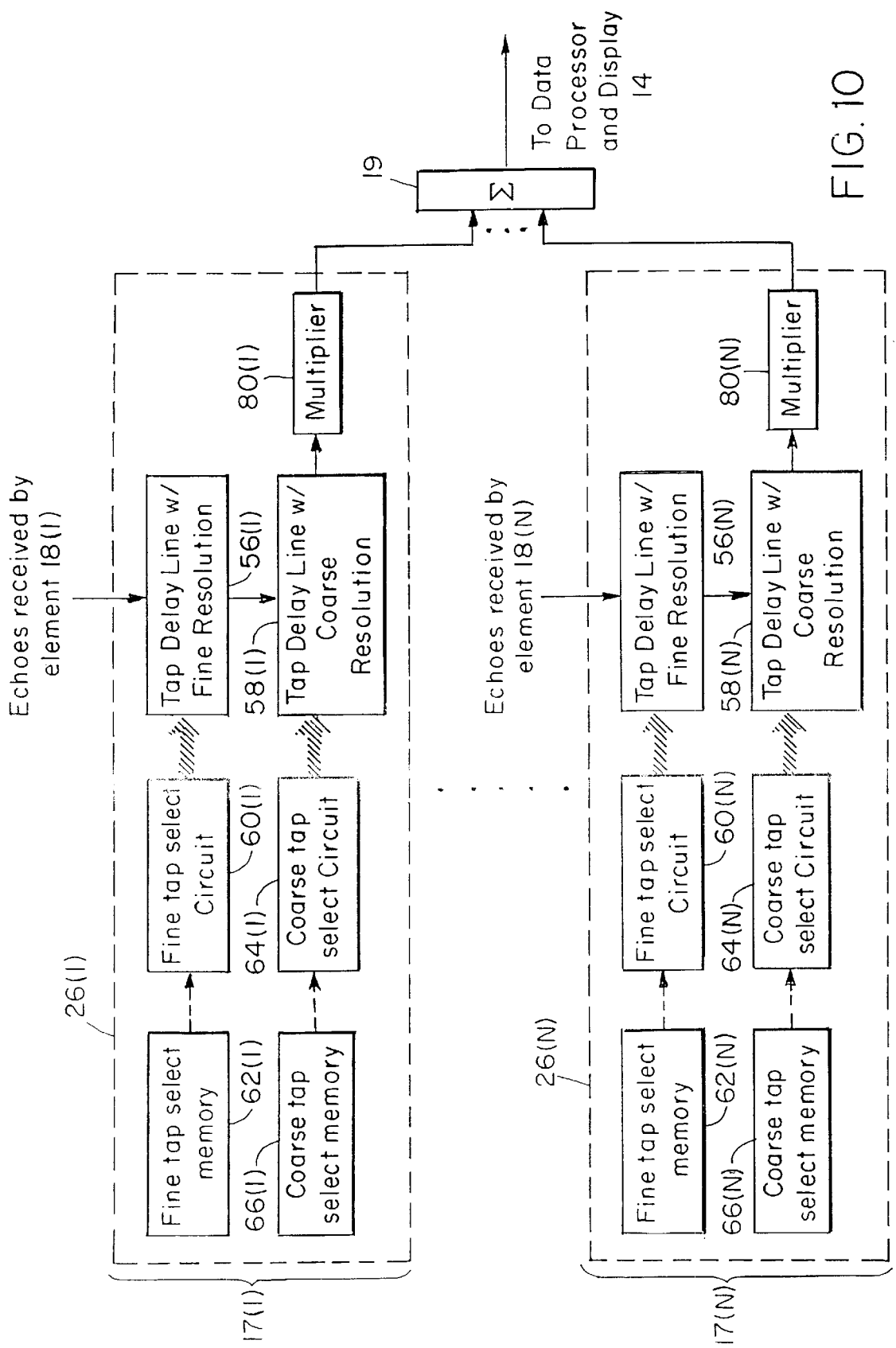
FIG. 10 shows an operational block diagram of an alternative embodiment of the present invention in which the selected outputs of each beam forming and focusing circuit are applied to respective multiplier circuits.

An operational block diagram of another alternative embodiment of the beam forming circuitry 26 of the present invention is shown in FIG. 10, in which the selected outputs of each coarse delay line 58(1)–58(N) are applied to respective multiplier circuits 80(1)–80(N) prior to being provided to the summation circuit 19. An exemplary multiplier for use in the aforementioned embodiment of the beam forming circuits is described in co-pending U.S. patent application Ser. No. 08/388,170, entitled "Single-Chip Adaptive Filter Utilizing Updatable Weighting Techniques," filed Feb. 10, 1995 by Alice M. Chiang, which is incorporated herein by reference.

The configuration of the multipliers 80 will accommodate the use of apodization techniques, such as incorporating a conventionally known Hamming weighting or code at the receiving array to reduce the sidelobe level and generate better quality imagery. Similar to the embodiment shown in FIG. 8, latch circuits 70(1)–70(N) may be included in association with each of the beam forming circuits 26(1)–26(N) in order to control the latching of the tap select position for the fine delay lines 56(1)–56(N). Conventional apodization and Hamming weighting techniques are described in, for example, Gordon S. Kino, *Acoustic Waves: Devices, Imaging, and Analog Signal Processing*, Prentice-Hall, Inc. (1987), which is incorporated herein by reference.

Figure 11:
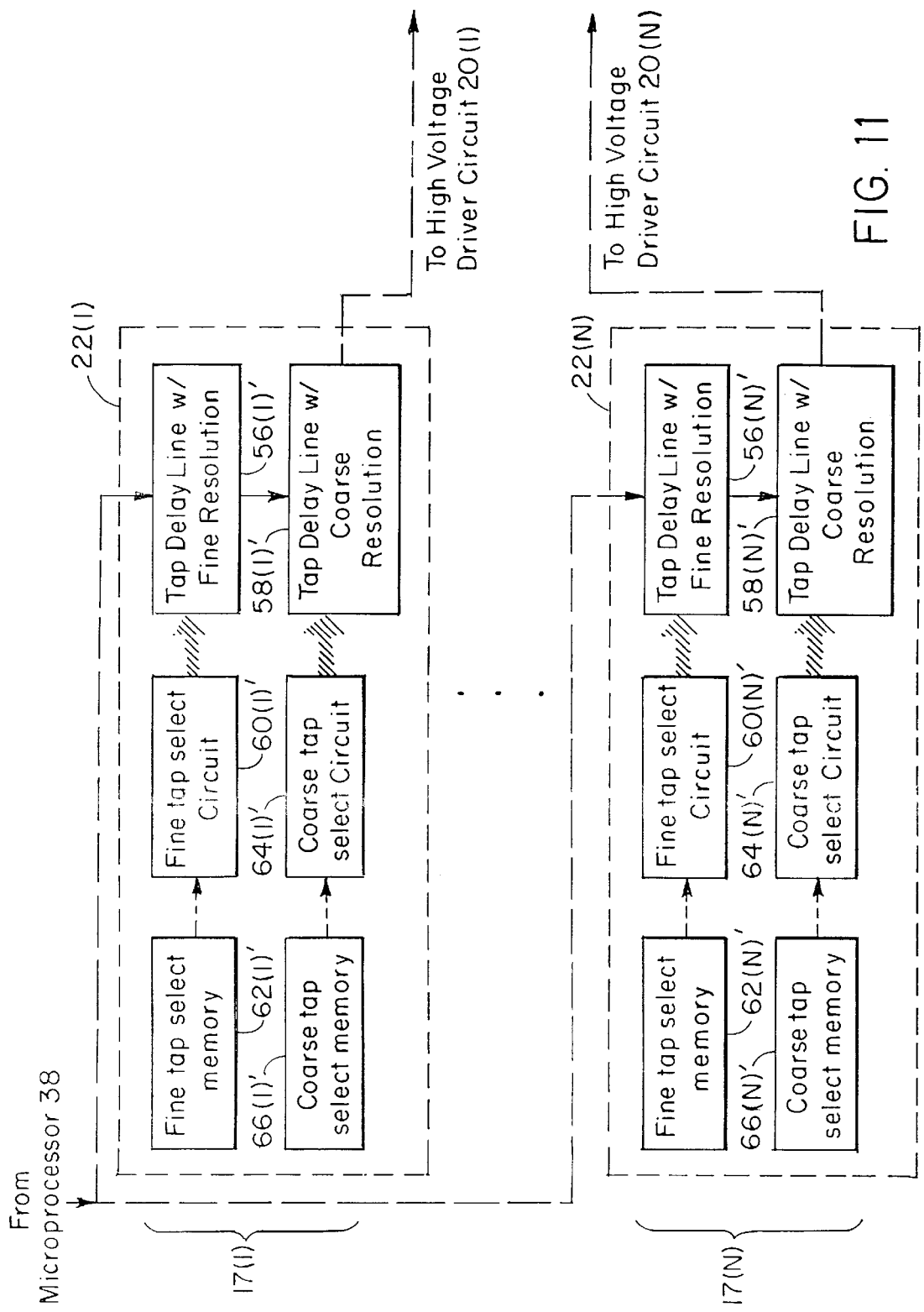
FIG. 11 shows an operational block diagram of an alternative embodiment of the present invention in which a plurality of beam forming and focusing circuits of the present invention are arranged for operation in a transmission mode.

FIG. 11 shows an operational block diagram of the cascaded dual tapped CCD delay lines used in pulse synchronizers 22(1)–22(N) to introduce delay into individual transmitted signals in the transmit mode of the ultrasound system 10 of the present invention. Each pulse synchronizer circuit 22(1)–22(N) includes two cascading tapped delay lines 56(1)'–56(N)' and 58(1)'–58(N)'. The first delay line 56' in each processing channel provides a fine time delay for the signals to be transmitted, while the cascaded second delay line 58' provides a coarse time delay. Each fine delay line has an associated programmable fine tap select circuit 60(1)'–60(N)', which receive tap select addresses from respective fine tap select memory units 62(1)'–62(N)'. Each coarse delay line has an associated programmable coarse tap select circuit 64(1)'–64(N)', which receive tap select addresses from respective fine tap select memory units 66(1)'–66(N)'. The tap-select circuits are operable for effecting a variable delay time as a function of tap location.

During the operation of the pulse synchronizers 22 in the transmission mode, signals which are provided from the microprocessor 38 via the memory 42 (see FIG. 4), are applied continuously to the inputs of each processing channel 17(1)–17(N). The input signals to each processing channel are converted into a sequence of sampled data for initial propagation through the respective fine tapped delay line 56. In an exemplary configuration of the pulse synchronizer circuits 22(1)–22(N) using CCD delay lines, the input signals to each of the processing channels are converted to a sequence of charge packets for subsequent propagation through the fine and coarse delay lines.

At a predetermined time which is dependent on the tap location selected by the imaging system, a delayed sample is either destructively or nondestructively sensed from the selected tap of the fine delay line 56. The delayed sample is in turn input to the front end of the corresponding coarse delay line 58. The selected delay samples thereafter propagate through the coarse delay line, and are again sensed at a properly selected tap location corresponding to a predetermined time delay designated in accordance with the operation of the microprocessor 38 of the ultrasound imaging system 10. The sensed sampled data from each of the coarse delay lines 58(1)–58(N) are then converted and transmitted as ultrasonic pulse signals by the corresponding transducer elements 18(1)–18(N). In accordance with a preferred embodiment of the present invention, the fine and coarse delay lines of each pulse synchronizer circuit have differing clock rates. In the transmission mode, the fine delay line can be clocked at either a higher or lower rate than that of the coarse delay line in order to accomplish the desired beam forming and focusing.

In another embodiment of the invention, an adaptive beam forming imaging (ABI) technique is used in both the beam forming circuits 26 and the pulse synchronizer circuits 22 to introduce the appropriate delays to produce a focused image. The adaptive beam forming technique improves image quality and spatial resolution by suppressing artifacts due to scattering sources and clutter in the sidelobes of the transducer array response. This adaptive beam forming circuitry can also be implemented on a single chip.

ABI is a model-based approach to image reconstruction derived from superresolution techniques. ABI offers improvements in resolution and reduction in sidelobes, clutter, and speckle. Superresolution algorithms modified for imaging include the two-dimensional maximum likelihood method (MLM) and two-dimensional multiple-signal classification (MUSIC). ABI incorporates models for the desired backscatter (amplitude and phase), providing better detection performance than conventional imaging methods.

Figure 12:
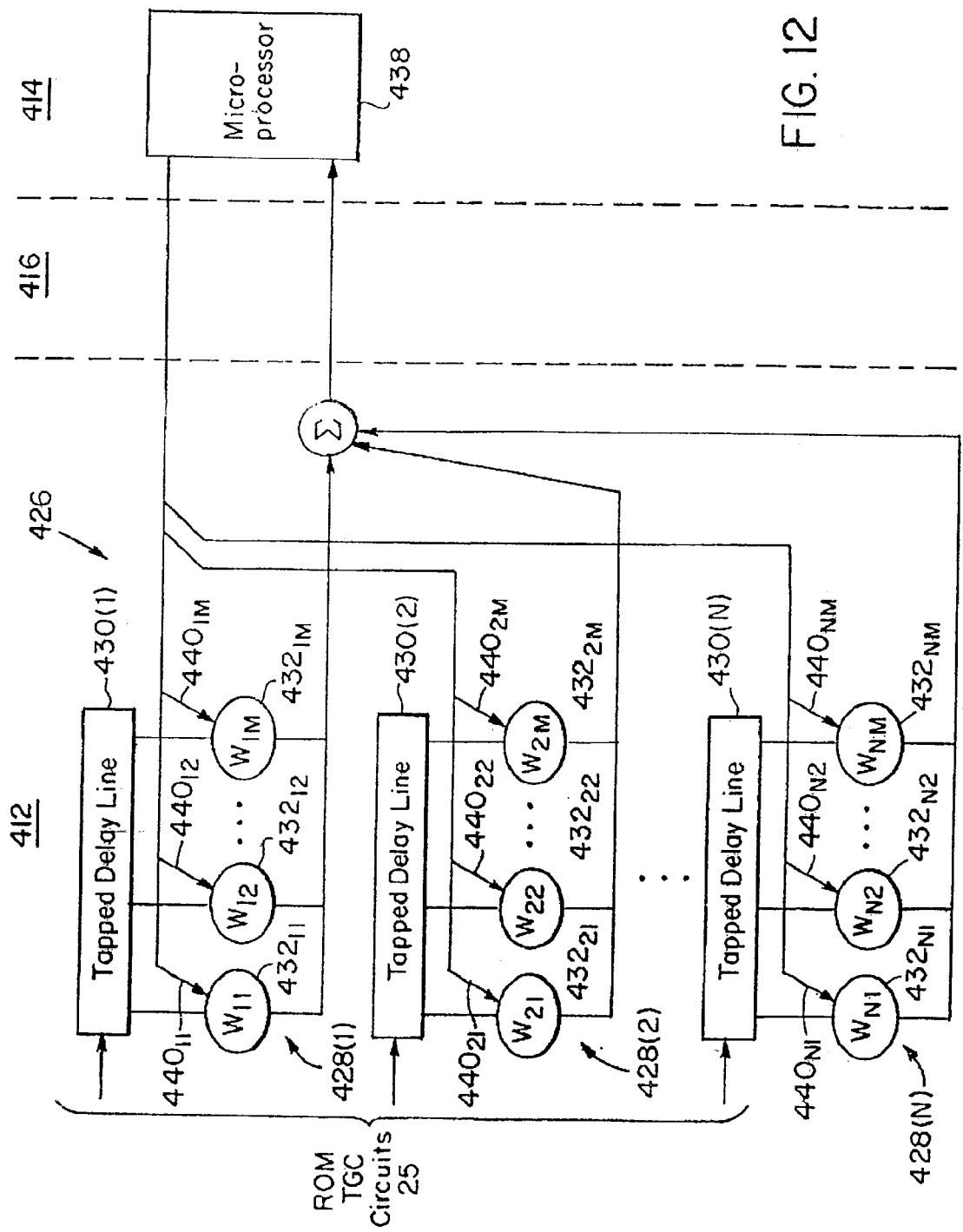
FIG. 12 is a schematic functional block diagram of one preferred embodiment of adaptive beam forming circuitry in accordance with the present invention.

FIG. 12 is a schematic functional block diagram depicting one embodiment of adaptive beam forming circuits 426 located in the scan head 412 in accordance with the present invention. In the adaptive beam forming circuits 426, individual multiplier weights of the finite impulse response (FIR) filter are controlled by a feedback loop, in such a way as to reduce clutter and interference or finite impulse response (FIR) filters. In either case, the adaptive circuits are used to remove clutter and interference such as that caused by ultrasonic signal in the sidelobes of the array pattern to produce an image with much higher accuracy and resolution.

Each processing channel 428(1)–428(N) of the beam forming circuits 426 receives a signal from a respective time-varying gain control (TGC) circuit 25 at a respective tapped delay line 430. The beam forming circuits 426 includes N processing channels 428, one for each transducer in the array 18. Signals tapped off of each tapped delay line 430 are received by a set of weighted multiplying D/A converters 432. Each processing channel k includes M weighted multipliers 432, labelled $432_{k1}$–$432_{kM}$. The weights of the multipliers 432 are set to generate an output signal from each processing channel which is summed at a summing node 419. The summed signal is forwarded over the system cable 416 to the system control circuit such as the microprocessor 438 in the data processing and display unit 414. The microprocessor 438 analyzes the signal for known characteristics of such effects as clutter, sidelobes and interference. In response to detecting such effects, the microprocessor 438 generates control signals used to drive the multiplier weights 432 to adjust the signals to eliminate these effects from the output signal and forwards the control signals to the multipliers via the system cable 416 on lines 440. Thus, the adaptive beam forming circuitry comprises a feedback circuit which alters received signals from a tapped delay line of each channel prior to summation of the signals. The summed signal is sensed and correction signals based on the sensing are forwarded in the feedback loop to the multipliers to correct the summed signal.

The ABI results in an image of much higher resolution and overall quality than is obtainable in prior systems. The ABI technique results in at least two to three times better resolution than that provided by conventional imaging techniques. As an example, in conventional ultrasound, at a frequency of 5 MHz, a resolution of about 1 mm can be obtained. Using ABI techniques, a lateral resolution of approximately 300 $\mu$m is obtained.

As described above, the ultrasound signal is received and digitized in its natural polar (r, $\theta$) form. For display, this representation is inconvenient, so it is converted into a rectangular (x,y) representation for further processing. The rectangular representation is digitally corrected for the dynamic range and brightness of various displays and hard-copy devices. The data can also be stored and retrieved for redisplay. In making the conversion between polar and rectangular coordinates, the (x,y) values must be computed from the (r, $\theta$) values since the points on the (r, $\theta$) array and the rectangular (x,y) grid are not coincident.

In prior scan conversion systems, each point on the (x,y) grid is visited and its value is computed from the values of the four nearest neighbors on the (r, $\theta$) array by simple linear interpolation. This is accomplished by use of a finite state machine to generate the (x,y) traversal pattern, a bidirectional shift register to hold the (r, $\theta$) data samples in a large number of digital logic and memory units to control the process and ensure that the correct asynchronously received samples of (r, $\theta$) data arrive for interpolation at the right time for each (x,y) point. This prior implementation can be both inflexible and unnecessarily complex. Despite the extensive control hardware, only a single path through the (x,y) array is possible. This means that full advantage of different ultrasound scan frequencies and, hence, imaging depth, cannot be taken. That is, different data are forced into the same format regardless of physical reality.

In the scan conversion circuitry 28 of the present invention (see FIG. 4), hardware complexity and cost are drastically reduced through the use of a number-theoretic scheme for reliably generating the (x,y) grid traversal path in natural order, i.e., using the (r, θ) samples as they are acquired. This approach provides greater flexibility and better fidelity to the actual medical data, as it permits the array traversals to be designed so that they do not impose an unnatural image reconstruction scheme. This scan conversion circuitry 28 of the present invention uses a Farey-sequence generator process, which generates the (x,y) coordinates in the order in which they are encountered in the scanning.

Assume that the system received the first two scan rays; it is desired to identify all the (x,y) integer pairs situated within the wedge for $0<y\leq L$. A process which uses a Farey sequences to generate all (x,y) pairs within two successive arrays with $0<y\leq L$ in the order of increasing angle is described here. The process exploits the fact that certain (x,y) pairs lie along the same angle, so it generates only (a,b) pairs which are mutually prime and then sets the rest of (x,y) pairs by (x,y)=n(a,b) for n=1, 2, . . . until (n+1) b>L. To better understand how this is accomplished, let us define a Farey sequence.

Definition: The sequence of rational numbers whose denominator does not exceed L, arranged in increasing numerical order, is called the Farey sequence of order L. If u/v is a fraction in lowest terms and $v \leq L$, we will call u/v a Farey fraction of order L. Therefore, Farey fraction is in lowest terms; thus, its numerator and denominator are mutually prime. The theory of Farey series is described in detail in G. H. Hardy and E. M. Wright, *An Introduction to the Theory of Numbers*, Oxford University Press, London 1938, pp. 23–24, which is incorporated herein by reference.

Of relevance to the present invention is the following relationship.

Let a/b, c/d, e/f be three successive Farey fractions of order L and let $$Z = \left[ \frac{L+b}{d} \right], \text{ where } [\ ] = \text{greatest integer function.} \quad (1)$$

Then $$e=Zc-a, f=Cd-b. \quad (2)$$

Equations 1 and 2 permit us to begin with any two successive Farey fractions and interate through all the rest within the slice.

Figure 13:
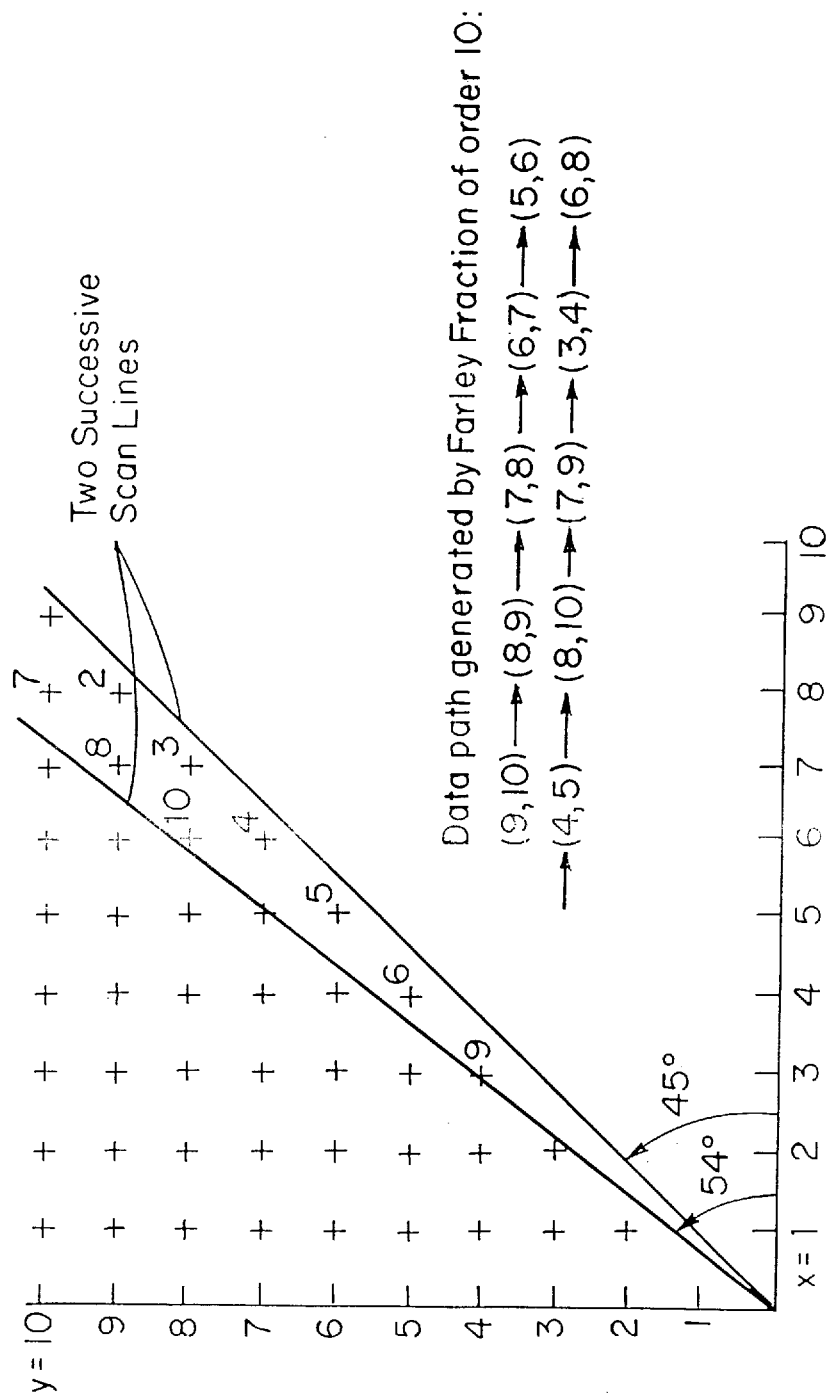
FIG. 13 is a schematic diagram showing the scan conversion process of the invention.

A simple example of using Farey fractions of order 10 to generate all the (x,y) display points within the 46°–54° arc on a 10×10 grid is shown in FIG. 13. Substituting the values for the first two successive Farey fractions of the order L=10, a=1, b=1, and c=L−1=9, d=L=10 into Equations 1 and 2, one obtains the next Farey fraction with e=8, f=9. Now, repeating the same calculation with a=9, b=10, and c=8, d=9, yields the next Farey fractions with e=7, f=8. It is straightforward to generate all the (x,y) pairs within the given arc. If the user wants to map the same rays into a finer display grid (for example, onto a 20×20 display points), we use the same routine but with L=20 i.e., use the Farey function of order 20 to generate all the (x,y) display points. Simple arithmetic will show that the (x,y)-pairs are (19,20), (18,19), (17,18), . . . As can be seen in FIG. 13, all the grid points within the two successive scan lines are generated in natural order of increasing angle, i.e., $$a\tan\frac{10}{9} < a\tan\frac{9}{8} < a\tan\frac{8}{7} < a\tan\frac{7}{6} <$$

$$a\tan\frac{6}{5} < a\tan\frac{5}{4} < a\tan\frac{9}{7} < a\tan\frac{4}{3}.$$

This characteristic allows a scan conversion system that automatically adapts to variation in scan angle $\phi_o$. Systems with programmable, non-uniformly spaced scan arrays are possible with the Farey sequence implementation. In one embodiment of the invention, the data processing and display unit 14 is programmed to carry out the scan conversion process.

As mentioned above, the ultrasound imaging system 10 of the present invention also includes a pulsed Doppler processor 36 which allows for generation of color flow maps. Thus, moving targets (particularly flowing blood) can be displayed, letting physicians see the body's inner functions without surgery.

Figure 14:
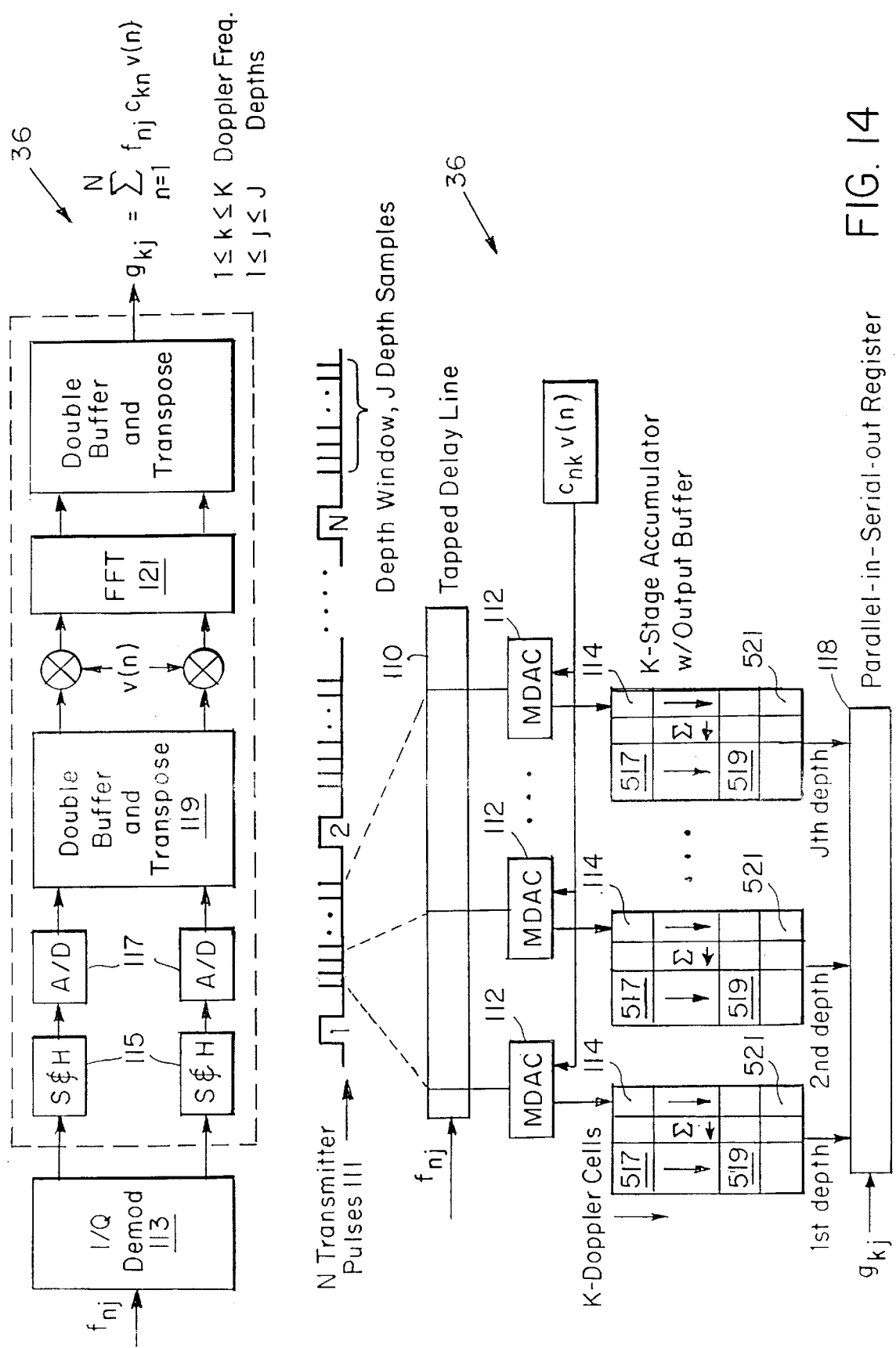
FIG. 14 is a schematic functional block diagram of a pulsed Doppler processing unit in accordance with the present invention.

The generic waveform 111 for pulsed Doppler ultrasound imaging is shown in FIG. 14. The waveform consists of a burst of N pulses with as many as J depth samples collected for each pulse in the burst. FIG. 14 also shows a block diagram of the pulsed Doppler signal processor 36 for this imaging technique, where the returned echoes received by each transducer are sampled and coherently summed prior to in-phase and quadrature demodulation at 113. The demodulated returns are converted to a digital representation at sample-and-hold circuits 115 and A/D converters 117, and then stored in a buffer memory 119 until all the pulse returns comprising a coherent interval are received. The N pulse returns collected for each depth are then read from memory, a weighting sequence, v(n), is applied to control Doppler sidelobes, and a N-point FFT is computed at 121. During the time the depth samples from one coherent interval are being processed through the Doppler filter, returns from the next coherent interval are arriving and are stored in a second input buffer.

The integrated Doppler processing device described herein performs all of the functions indicated in the dotted box of FIG. 14, except for A/D conversion, which is not necessary because the device provides the analog sampled data function. The remaining circuitry and the operation thereof is described in U.S. Pat. No. 4,464,726 to Alice M. Chiang, issued Aug. 7, 1984, entitled "charge Domain Parallel Processing Network," which is incorporated herein by reference. This pulsed-Doppler processor (PDP) device has the capability to compute a matrix-matrix product, and therefore has a broad range of capabilities. The device computes the product of two real valued matrices by summing the outer products formed by pairing columns of the first matrix with corresponding rows of the second matrix.

In order to describe the application of the PDP to the Doppler filtering problem, we first cast the Doppler filtering equation into a sum of real-valued matrix operations. The Doppler filtering is accomplished by computing a Discrete Fourier Transform (DFT) of the weighted pulse returns for each depth of interest. If we denote the depth-Doppler samples g(k,j), where k is the Doppler index, $0 \leq k \leq N-1$, and j is the depth index, then $$g(k,j) = \sum_{n=0}^{N-1} v(n)f(n,j)\exp(-j2\pi kn/N) \quad (3)$$

The weighting function can be combined with the DFT kernel to obtain a matrix of Doppler filter transform coefficients with elements given by $$w(k,n) = w_k n = v(n) \exp(-j2\pi kn/N) \quad (4)$$

The real and imaginary components of the Doppler filtered signal can now be written as $$g_{r,kj} = \sum_{n=0}^{N-1} (w_{r,kn} f_{r,nj} - w_{i,kn} f_{i,nj}) \quad (5)$$

$$g_{i,kj} = \sum_{n=0}^{N-1} (w_{r,kn} f_{i,nj} + w_{i,kn} f_{r,nj}) \quad (6)$$

In equations 5 and 6, the indices of the double-indexed variables may all be viewed as matrix indices. Therefore, in matrix representation, the Doppler filtering can be expressed as matrix product operation. It can be seen that the PDP device can be used to perform each of the four matrix multiplications thereby implementing the Doppler filtering operation.

The PDP device 36 of the invention includes a J-stage CCD tapped delay line 110, J CCD multiplying D/A converters (MDACs) 112, J×K accumulators 114, J×K Doppler sample buffer 517, and a parallel-in-serial out (PISO) output shift register 118. The MDACs share a common 8-bit digital input on which elements from the coefficient matrix are supplied. The tapped delay line 110 performs the function of a sample-and-hold, converting the continuous-time analog input signal to a sampled analog signal.

In operation, the device 36 functions as follows: either the real or imaginary component of the returned echo is applied to the input of the tapped delay line 110. At the start of the depth window, the video is sampled at the appropriate rate and the successive depth samples are shifted into the tapped delay line 110. Once the depth samples from the first pulse return interval (PRI) are loaded, each element in the first column of the transform coefficient matrix W is sequentially applied to the common input of the MDACs 112. The products formed at the output of each MDAC 112 are loaded into a serial-in-parallel-out (SIPO) shift register 521. The collection of J×K products computed in this fashion represent an outer product matrix. These products are transferred from the SIPOs to CCD summing wells which will accumulate the outer product elements from subsequent PRIs. The process is repeated until all pulse returns (rows of F) have been processed.

At this point, each group of K accumulators 114 holds the K Doppler samples for a specific depth cell. The Doppler samples are simultaneously clocked into the accumulator output PISO shift registers 519. These registers act as a buffer to hold the J×K depth-Doppler samples, so processing can immediately begin on the next coherent interval of data. Finally, the accumulator shift registers 521 are clocked in parallel transferring all the depth samples for a given Doppler cell into the device output PISO shift register 118. Samples are serially read out of the PDP device in range order, which is the desired order for flow-map display.

A prototype PDP-A device for 16-depth samples has been fabricated. The PDP-A can be used to process returns of a burst waveform with as many as 16 range samples collected for each pulse in the burst. The capability of detecting weak moving targets in the presence of a strong DC clutter has been successfully demonstrated by the prototype PDP device.

Figure 15:
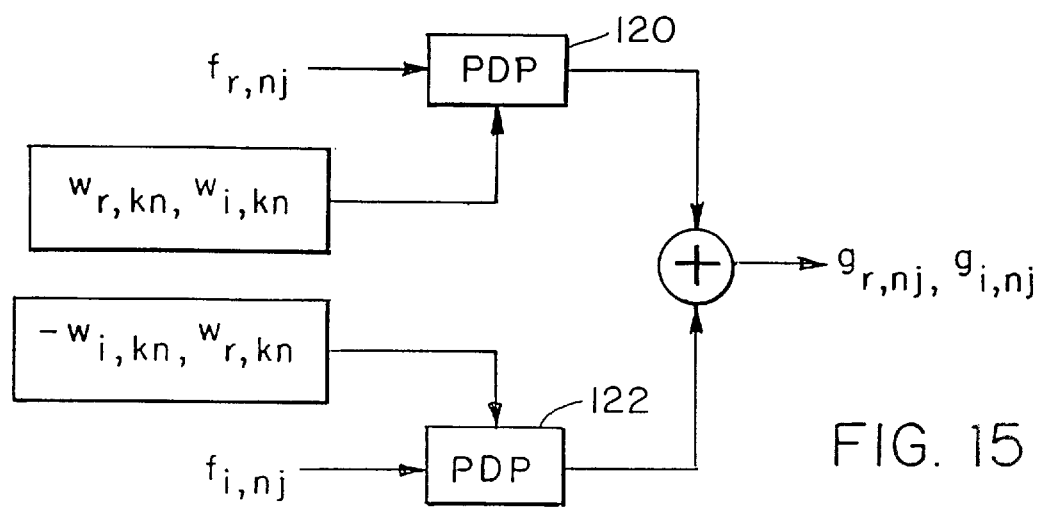
FIG. 15 is a schematic block diagram of a color flow map chip implementation using dual pulsed Doppler processors in accordance with the present invention.

A two-PDP implementation for color flow mapping in an ultrasound imaging system is shown in FIG. 15. In this device, during one PRI the top PDP component 120 computes all the terms of the form $w_r f_r$ and $w_i f_r$ as shown in equations 5 and 6, while the bottom component 122 computes terms of the form $-w_i f_i$ and $w_r f_i$. The outputs of each component are then summed to alternately obtain $g_r$ and $g_i$.

As mentioned above, the imaging system of the invention also includes video compression circuitry 34 which conditions the data and transforms it into a compressed format to permit it to be transferred to a remote location. In a preferred embodiment, the video data compression circuitry is of the type described in U.S. Pat. Nos. 5,126,962 to Alice M. Chiang, issued Jun. 30, 1992, entitled "Discrete Cosine Transform Processing System," and 5,030,953 to Alice M. Chiang, issued Jul. 9, 1991, entitled "Charge Domain Block Matching Processor," both of which are incorporated herein by reference.

Figure 16:
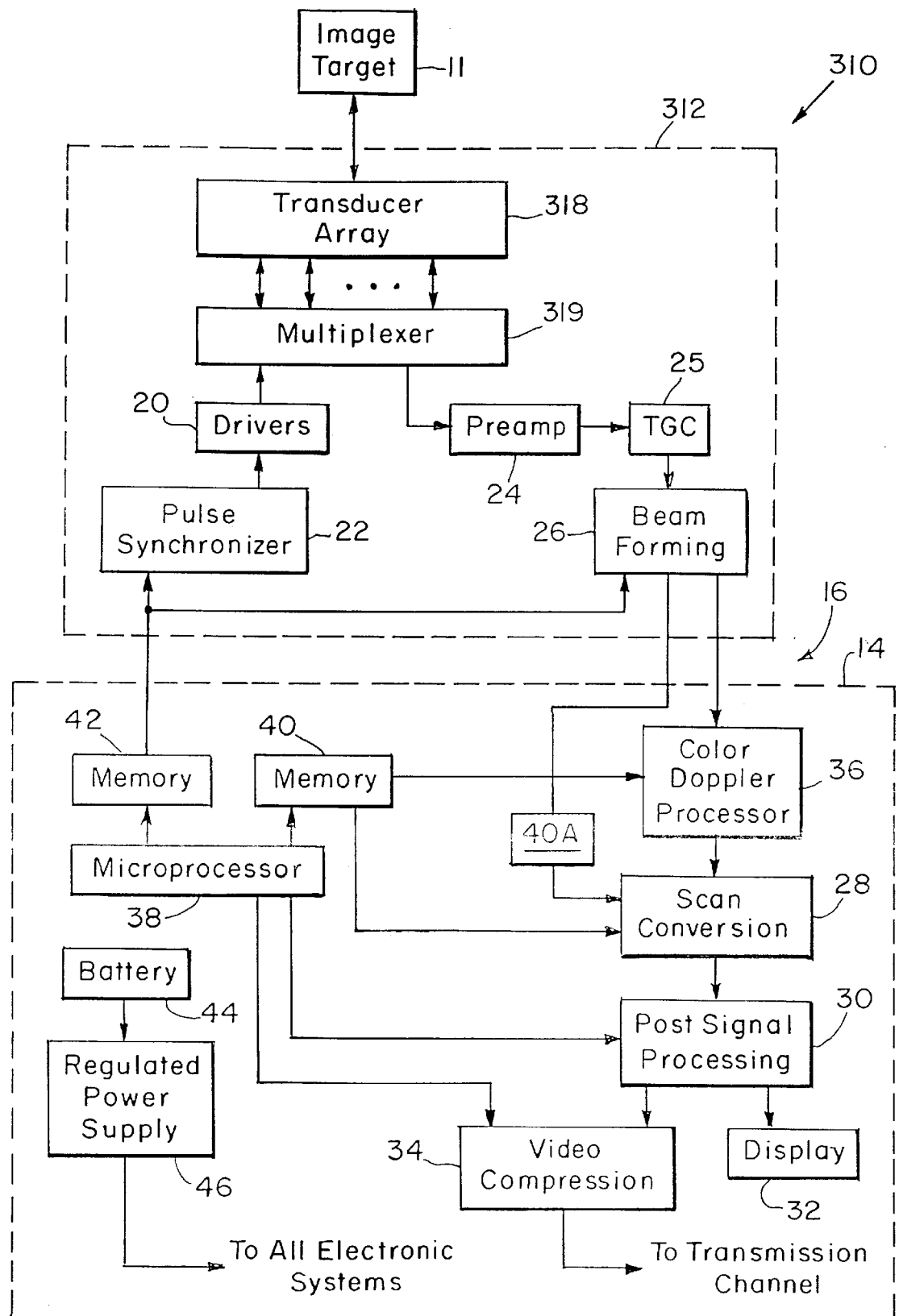
FIG. 16 is a schematic functional block diagram of an alternative preferred embodiment of the ultrasound imaging system of the invention.

FIG. 16 is a schematic functional block diagram of an alternative preferred embodiment of the ultrasound imaging system of the invention. In the embodiment of FIG. 19, a multiplexer 319 is added to the scan head 312 between the ultrasonic transducer array 318 and the drivers 20 and preamplification circuitry 24. In this embodiment, signals are processed from only a portion of the transducer array 318 at any given time. For example, with a 128-element array 318, in one embodiment, only 64 elements will be processed at a time. The multiplexer 319 is used to route the 64 signals to the preamplification 24 and subsequent circuits. The multiplexer 319 is also used to route the driver pulses from the drivers 20 to the 64 elements of the array 318 currently being driven. In this embodiment, referred to herein as the sub-aperture scanning embodiment, circuit complexity is substantially reduced since processing channels need only be provided for the number of elements which are being processed, in this example, 64. Images are formed in this embodiment by scanning across the transducer array 318 and selectively activating groups of adjacent elements to transmit and receive ultrasonic signals.

Figure 17A:
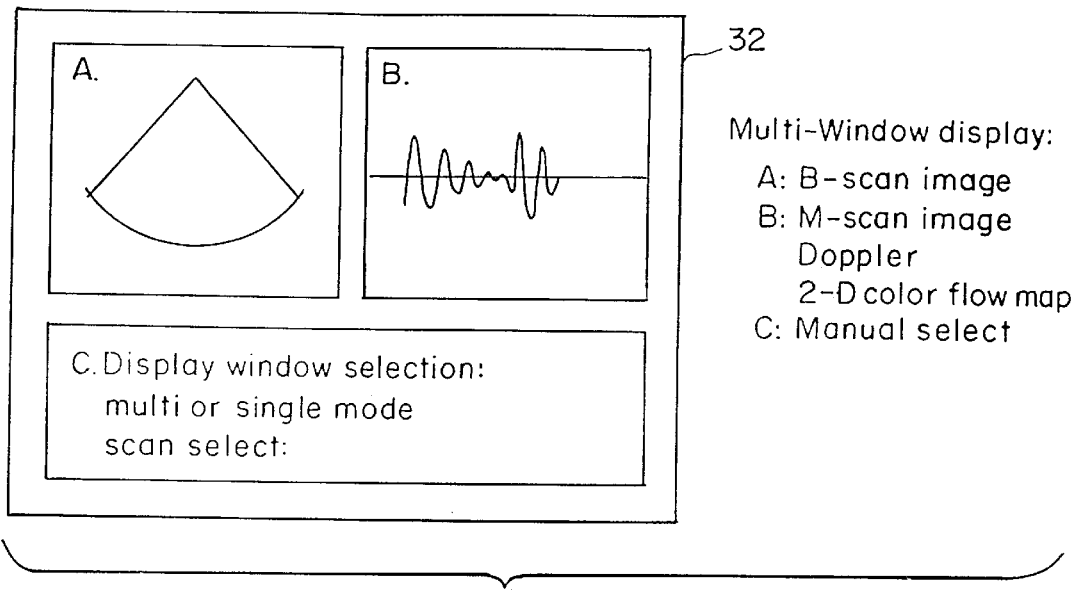
FIGS. 17A and 17B are schematic pictorial views of two user-selectable display presentation formats used in the ultrasound imaging system of the invention.
Figure 17B:
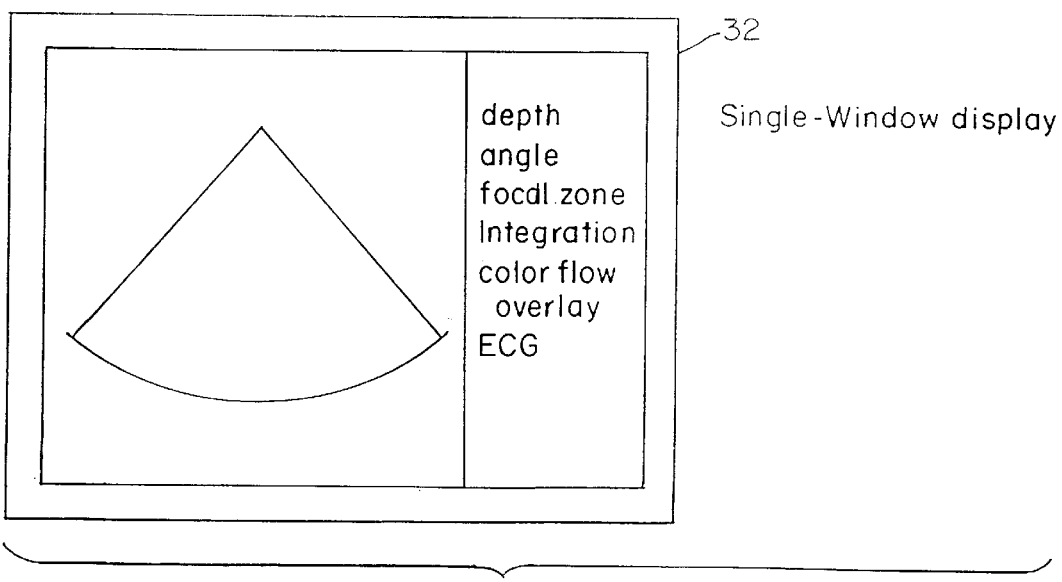

FIGS. 17A and 17B are schematic pictorial views of display formats which can be presented on the display 32 of the invention. Rather than storing a single display format as is done in prior ultrasound imaging systems, the system of the present invention has multiple window display formats which can be selected by the user. FIG. 17A shows a selectable multi-window display in which three information windows are presented simultaneously on the display. Window A shows the standard B-scan image, while window B shows an M-scan image of a Doppler two-dimensional color flow map. Window C is a user information window which communicates command selections to the user and facilitates the user's manual selections. FIG. 17B is a single-window optional display in which the entire display is used to present only a B-scan image.

While this invention has been particularly shown and described with references to preferred embodiments thereof, it will be understood by those skilled in the art that various changes in form and details may be made therein without departing from the spirit and scope of the invention as defined by the appended claims.

The invention claimed is:

1. A portable ultrasound imaging system comprising:
    a hand-held scan head housing that receives reflected ultrasonic signals from a region of interest, the hand-held scan head housing comprising:
        an array of ultrasonic transducers that receives the reflected ultrasonic signals from the region of interest and converts the received ultrasonic signals into electrical signals, and
        beam forming circuitry including a delay circuit within the scan head housing that receives the electrical signals from the ultrasonic transducers;
    a summing circuit that sums the delayed electrical signals;

a portable computer system comprising:
- a system housing;
- processing circuitry within the system housing that receives and processes a digital electronic representation of the region of interest from the scan head housing;
- scan conversion circuitry within the system housing which converts polar coordinates of the digital electronic representation to rectangular coordinates,
- a display that displays an image of the region of interest,
- a keyboard that provides a user interface, and
- a battery within the system housing that powers the portable computer system and the scan head; and
- a cable connecting the scan head housing to the portable computer system housing such that a digital electronic representation of the region of interest is received by the portable computer system through the cable.

2. The portable ultrasound imaging system of claim 1 wherein the beam forming circuitry of the scan head comprises a feedback circuit that provides a correction signal which alters at least one of the electrical signals before the electrical signals are combined into the electrical representation of the region of interest.

3. The ultrasound imaging system of claim 1 wherein the beam forming circuitry of the scan head comprises programmable tapped delay line for each ultrasonic transducer to dynamically focus the electrical signals generated by the ultrasonic transducers.

4. The ultrasound imaging system of claim 3 wherein each delay line comprises a charge-coupled device.

5. The ultrasound imaging system of claim 1 wherein the hand-held scan head further comprises pulsed synchronization circuitry that provides timing signals to the array of ultrasonic transducers to time ultrasonic signals transmitted into the region of interest by the ultrasonic transducers.

6. The ultrasound imaging system of claim 1 wherein the scan head further comprises amplification circuitry that amplifies the electrical signals from the ultrasonic transducers and couples the amplified signals to the beam forming circuitry.

7. The ultrasound imaging system of claim 1 wherein the scan head further comprises driver circuitry that generates signals to drive the ultrasonic transducers to transmit the ultrasonic signals.

8. The ultrasound imaging system of claim 1 wherein the scan head further comprises memory circuitry that stores data used to control the beam forming circuitry.

9. The ultrasound imaging system of claim 1 wherein the scan head further comprises gain control circuitry that controls voltage levels of the electrical signals from the ultrasonic transducers.

10. The ultrasound imaging system of claim 1 further comprising video data compression circuitry that compresses image data such that the image data can be transferred to a remote location.

11. The ultrasound imaging system of claim 1 further comprising pulsed Doppler processing circuitry that processes data to generate an image of a moving object in the region of interest.

12. The ultrasound imaging system of claim 1 wherein the beam forming circuitry of the scan head comprises a programmable tapped delay line for each ultrasonic transducer to dynamically focus the electrical signals generated by the ultrasonic transducers.

13. The ultrasound imaging system of claim 12 wherein the delay line comprises a charge-coupled device.

14. A method of examining a region of interest with an ultrasound imaging system comprising:
- providing a hand-held scan head that receives reflected ultrasonic signals from the region of interest, the hand-held scan head having a housing in which are located (i) an array of ultrasonic transducers for receiving the reflected ultrasonic signals from the region of interest and converting the received ultrasonic signals into electrical signals and (ii) beam forming circuitry that delays and combines the electrical signals from the ultrasonic transducers into a combined signal;
- providing a portable computer system having (i) processing circuitry that receives and processes the combined signal, (ii) scan conversion circuitry which converts polar coordinates of the combined signal to rectangular coordinates, (iii) a display that displays an image of the region of interest, (iv) a keyboard that provides a user interface, and (v) a battery that powers the portable computer system and the scan head;
- providing a cable connecting the scan head to the portable computer system;
- detecting ultrasonic signals from a region of interest and generating a combined signal; and
- forwarding the combined signal over the cable to the portable computer system.

15. The method of claim 14 wherein the step of providing a hand-held scan head comprises providing the beam forming circuitry with a feedback circuit that provides a correction signal which alters at least one of the electrical signals before the electrical signals are combined into the electrical representation of the region of interest.

16. The method of claim 14 wherein the step of providing a hand-held scan head comprises providing the beam forming circuitry with a programmable tapped delay line for each ultrasonic transducer to dynamically focus the electrical signals generated by the ultrasonic transducers.

17. The method of claim 16 wherein each delay line comprises a charge-coupled device.

18. The method of claim 14 further comprising the step of providing pulse synchronization circuitry within the housing of the scan head to provide timing signals to the array of ultrasonic transducers to time ultrasonic signals transmitted into the region of interest by the ultrasonic transducers.

19. The method of claim 14 further comprising:
- amplifying the electrical signals from the ultrasonic transducers; and
- coupling the amplified signals to the beam forming circuitry.

20. The method of claim 14 further comprising storing data used to control the beam forming circuitry in memory within the housing of the scan head.

21. The method of claim 14 further comprising controlling voltage levels of the electrical signals from the ultrasonic transducers with gain control circuitry.

22. A portable ultrasound imaging system comprising:
- a hand-held scan head housing that transmits an ultrasonic signal and that receives reflected ultrasonic signals from a region of interest, the hand-held scan head housing comprising:
  - an array of ultrasonic transducers that receives the reflected ultrasonic signals from the region of interest and converts the received ultrasonic signals into electrical signals, and
  - a charge coupled device having beam forming circuitry that delays and combines the electrical signals from the ultrasonic transducers into a combined signal;

a portable computer system weighing less than 10 pounds and comprising:
  a microprocessor that controls the scan head,
  digital signal processing circuitry that receives and processes the combined signal,
  scan conversion circuitry that converts the combined signal to rectangular coordinates,
  a flat panel display that displays an image of the region of interest,
  a control panel that provides a user interface; and
a cable connecting the scan head to the portable computer system.

23. The system of claim 22 wherein the scan head has a temperature of less than 40 degrees centigrade during scanning of the region of interest.

24. The system of claim 23 further comprising an interface circuit connected between the scan head housing and the portable computer.

25. A portable ultrasound imaging system comprising:
  a hand-held housing that receives reflected ultrasonic signals from a region of interest, the hand-held housing comprising:
    a first array of ultrasonic transducers for receiving the reflected ultrasonic signals from the region of interest and converting the received ultrasonic signals into electrical signals, and
    beam forming delay circuitry that delays the electrical signals from the ultrasonic transducers and generates an electronic representation of the region of interest;
  a portable computer system comprising:
    processing circuitry that receives and processes a digital representation of the region of interest;
    scan conversion circuitry which converts polar coordinates of the combined signal to rectangular coordinates,
    a display that displays an image of the region of interest,
    a keyboard that provides a user interface, and
    a battery that powers the portable computer system and the scan head;
  an interface circuit connected to the portable computer and the beam forming delay circuitry, the interface circuit having a controller that generates the digital representation of the region of interest; and
  a cable connecting the scan head to the interface circuit.

26. The portable ultrasound imaging system of claim 25 wherein the beam forming circuitry of the scan head comprises a feedback circuit that provides a correction signal which alters at least one of the electrical signals before the electrical signals are combined into the electrical representation of the region of interest.

27. The ultrasound imaging system of claim 25 wherein the hand-held scan head further comprises pulsed synchronization circuitry that provides timing signals to the array of ultrasonic transducers to time ultrasonic signals transmitted into the region of interest by the ultrasonic transducers.

28. The ultrasound imaging system of claim 25 wherein the scan head further comprises amplification circuitry that amplifies the electrical signals from the ultrasonic transducers and couples the amplified signals to the beam forming circuitry.

29. The ultrasound imaging system of claim 25 wherein the scan head further comprises driver circuitry that generates signals to drive the ultrasonic transducers to transmit the ultrasonic signals.

30. The ultrasound imaging system of claim 25 wherein the scan head further comprises memory circuitry that stores data used to control the beam forming circuitry.

31. The ultrasound imaging system of claim 25 further comprising a second scan head housing having a second transducer array different from the first array and a second beam former, the second scan head housing being connectable to the system housing.

32. The ultrasound imaging system of claim 25 further comprising pulsed Doppler processing circuitry that processes data to generate an image of a moving object in the region of interest.

* * * * *